(12) United States Patent
Lancaster et al.

(10) Patent No.: US 9,983,209 B2
(45) Date of Patent: May 29, 2018

(54) METHOD OF DIAGNOSING, TREATING AND DETERMINING PROGRESSION AND SURVIVAL OF CANCER CELLS USING BCL-2 ANTAGONIST OF CELL DEATH (BAD) PATHWAY GENE SIGNATURE

(71) Applicant: H. Lee Moffitt Cancer Center and Research Institute, Inc., Tampa, FL (US)

(72) Inventors: Johnathan M. Lancaster, Tampa, FL (US); Douglas C. Marchion, Seminole, FL (US); Yin Xiong, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 116 days.

(21) Appl. No.: 14/537,521

(22) Filed: Nov. 10, 2014

(65) Prior Publication Data
US 2015/0140124 A1 May 21, 2015

Related U.S. Application Data

(63) Continuation of application No. PCT/US2013/040583, filed on May 10, 2013.

(60) Provisional application No. 61/645,369, filed on May 10, 2012.

(51) Int. Cl.
| | |
|---|---|
| *G01N 33/574* | (2006.01) |
| *C12N 15/113* | (2010.01) |
| *C12Q 1/68* | (2018.01) |

(52) U.S. Cl.
CPC ... *G01N 33/57484* (2013.01); *C12N 15/1135* (2013.01); *C12Q 1/6886* (2013.01); *G01N 33/57407* (2013.01); *G01N 33/57415* (2013.01); *G01N 33/57419* (2013.01); *G01N 33/57442* (2013.01); *G01N 33/57492* (2013.01); *G01N 33/57496* (2013.01); *C12N 2310/14* (2013.01); *C12Q 2600/118* (2013.01); *C12Q 2600/158* (2013.01); *G01N 2800/52* (2013.01); *G01N 2800/60* (2013.01)

(58) Field of Classification Search
None
See application file for complete search history.

(56) References Cited

U.S. PATENT DOCUMENTS

| 7,871,769 B2 | 1/2011 | Baker et al. |
| 2004/0209290 A1 | 10/2004 | Cobleigh et al. |
| 2008/0108091 A1* | 5/2008 | Hennessy ............ G01N 33/574 435/7.23 |
| 2009/0311702 A1 | 12/2009 | Shak et al. |
| 2010/0233733 A1* | 9/2010 | Fantl .................. G01N 33/5011 435/7.23 |

FOREIGN PATENT DOCUMENTS

WO 2011088137 A2 7/2011

OTHER PUBLICATIONS

Bansal et al, Gynecol Oncol, 116:S10, Mar. 2010.*
Saadat et al, Oncol Res, 7:505-510, 1995.*
Jazaeri et al, Clin Cancer Res, 11:6300-6310, 2005.*
Jolliffe, Principal Component Analysis. 2 ed. New York: Springer; 2002.
Zha, et al., Serine phosphorylation of death agonist BAD in response to survival factor results in binding to 14-3-3 not BCL-X(L). Cell 1996;87: 619-28.
Kirschner, et al., Mutations of the gene encoding the protein kinase A type I-alpha regulatory subunit in patients with the Carney complex. Nat Genet 2000;26: 89-92.
Klumpp, et al., Protein phosphatase type 2C dephosphorylates BAD. Neurochem Int 2003;42: 555-60.
Efron and Tibshirani, Empirical bayes methods and false discovery rates for microarrays. Genet Epidemiol 2002;23: 70-86.
International Preliminary Report on Patentability for PCT/US2013/040583, filing date May 10, 2013, dated Nov. 11, 2014.
International Search Report and Written Opinion for PCT/US2013/040583, filing date of May 10, 2013, dated Aug. 12, 2013.
Marchion et al., BAD Phosphorylation Determines Ovarian Cancer Chemosensitivity and Patient Survival. Clinical Research Center, vol. 17, No. 19, pp. 6356-6366 (Oct. 1, 2011).
Youle and Strasser, The BCL-2 protein family: opposing activities that mediate cell death. Nat. Rev. Mol. Cell Biol., 2008; 9: pp. 47-59.
Danial, BAD: undertaker by night, candyman by day. Oncogene 2008;27 Suppl 1: S53-70.
Chen D.T. et al., Proliferative genes dominate malignancy-risk gene signature in histologically-normal breast tissue. Breast Cancer Res Treat. Jan. 2010; 119(2):335-46.
Yang, et al., Bad, a heterodimeric partner for Bcl-XL and Bcl-2, displaces Bax and promotes cell death. Cell 1995;80: 285-91.
Holmgreen, et al., Survival activity of Bcl-2 homologs Bcl-w and A1 only partially correlates with their ability to bind pro-apoptotic family members. Cell Death Differ 1999;6: 525-32.
Jia, et al., Subcellular distribution and redistribution of Bcl-2 family proteins in human leukemia cells undergoing apoptosis. Blood 1999;93: 2353-9.

(Continued)

*Primary Examiner* — Mark Halvorson
(74) *Attorney, Agent, or Firm* — Michele L. Lawson; Smith & Hopen, P.A.

(57) ABSTRACT

The present invention relates to the BAD pathway's influence on development, progression, chemo-sensitivity, and overall survival for multiple human cancers and its potential as a therapeutic target to increase chemo-sensitivity. BAD pathway expression was associated with the development and/or progression of breast, colon, and endometrial cancers, relapse-free survival from breast cancer, and overall survival from ovarian, colon, and brain cancers. Expression was also associated with in vitro sensitivity to a range of cytotoxic agents. pBAD levels were higher in cancer versus immortalized normal cells and chemo-resistant versus— sensitive cancer cells and associated with increased cell proliferation.

1 Claim, 39 Drawing Sheets

(56) References Cited

OTHER PUBLICATIONS

Datta, et al., 14-3-3 proteins and survival kinases cooperate to inactivate BAD by BH3 domain phosphorylation. Mol Cell 2000;6: 41-51.
Roy, et al., Bad targets the permeability transition pore independent of Bax or Bak to switch between Ca2+-dependent cell survival and death. Mol Cell 2009;33: 377-88.
Tan, et al., BAD Ser-155 phosphorylation regulates BAD/Bcl-XL interaction and cell survival. J Biol Chem 2000;275: 25865-9.
Zhou, et al., Growth factors inactivate the cell death promoter BAD by phosphorylation of its BH3 domain on Ser155. J Biol Chem 2000;275: 25046-51.
Engelman, Targeting PI3K signaling in cancer: opportunities, challenges and limitations. Nat Rev Cancer 2009;9: 650-62.
del Peso, et al., Interleukin-3-induced phosphorylation of BAD through the protein kinase Akt. Science 1997;278: 687-9.
Hanahan and Weinberg, Hallmarks of cancer: the next generation. Cell;144: 646-74.
Blume-Jensen, et al., The kit receptor promotes cell survival via activation of PI 3-kinase and subsequent Akt-mediated phosphorylation of Bad on Ser136. Curr Biol 1998;8: 779-82.
Harada, et al., Phosphorylation and inactivation of BAD by mitochondria-anchored protein kinase A. Mol Cell 1999;3: 413-22.
Lizcano, et al., Regulation of BAD by cAMP-dependent protein kinase is mediated via phosphorylation of a novel site, Ser155. Biochem J 2000;349: 547-57.
Virdee, et al., Phosphorylation of the pro-apoptotic protein BAD on serine 155, a novel site, contributes to cell survival. Curr Biol 2000;10: R883.

Robinson-White, et al., PRKAR1A inactivation leads to increased proliferation and decreased apoptosis in human B lymphocytes. Cancer Res 2006;66: 10603-12.
Lammers and Lavi, Role of type 2C protein phosphatases in growth regulation and in cellular stress signaling. Crit Rev Biochem Mol Biol 2007;42: 437-61.
Konishi, et al., Cdc2 phosphorlaytion of BAD links the cell cycle to the cell death machinery. Mol Cell 2002;9: 1005-16.
Harley, et al., Phosphorylation of Mcl-1 by CDK1-cyclin B1 initiates its Cdc20-dependent destruction during mitotic arrest. EMBO J;29: 2407-20.
Ma, et al., Gene expression profiles of human breast cancer progression. Proc Natl Acad Sci U S A 2003;100: 5974-9.
Nutt, et al., Gene expression-based classification of malignant gliomas correlates better with survival than histological classification. Cancer Res. Apr. 1, 2003;63(7):1602-7.
Smith, et al., Experimentally derived metastasis gene expression profile predicts recurrence and death in patients with colon cancer. Gastroenterology;138: 958-68.
Wang, et al., Gene-expression profiles to predict distant metastasis of lymph-node-negative primary breast cancer. Lancet 2005;365: 671-9.
Chanrion M, et al., A gene expression signature that can predict the recurrence of tamoxifen-treated primary breast cancer. Clin Cancer Res 2008;14: 1744-52.
Tusher VG, et al., Significance analysis of microarrays applied to the ionizing radiation response. Proc Natl Acad Sci U S A 2001;98: 5116-21.

* cited by examiner

| Probe Set ID | Gene Title | Gene Symbol | up/down |
|---|---|---|---|
| Carboplatin | P<0.001 | | |
| 213950_s_at | Protein phosphatase 3 (formerly 2B), catalytic subunit, gamma isoform | PPP3CC | down |
| 208743_s_at | tyrosine 3-monooxygenase/tryptophan 5-monooxygenase activation protein, beta polypeptide | YWHAB | up |
| 203213_at | cell division cycle 2, G1 to S and G2 to M | CDC2 | up |
| 208652_at | protein phosphatase 2 (formerly 2A), catalytic subunit, alpha isoform | PPP2CA | up |
| 200746_s_at | guanine nucleotide binding protein (G protein), beta polypeptide 1 | GNB1 | down |
| 204566_at | protein phosphatase 1D magnesium-dependent, delta isoform | PPM1D | down |
| 210996_s_at | tyrosine 3-monooxygenase/tryptophan 5-monooxygenase activation protein, epsilon polypeptide | YWHAE | down |
| 200693_at | tyrosine 3-monooxygenase/tryptophan 5-monooxygenase activation protein, theta polypeptide | YWHAQ | down |
| 212249_at | phosphoinositide-3-kinase, regulatory subunit 1 (p85 alpha) | PIK3R1 | down |
| 205867_at | protein tyrosine phosphatase, non-receptor type 11 (Noonan syndrome 1) | PTPN11 | down |
| 204842_x_at | protein kinase, cAMP-dependent, regulatory, type II, alpha | PRKAR2A | up |
| 210317_s_at | tyrosine 3-monooxygenase/tryptophan 5-monooxygenase activation protein, epsilon polypeptide | YWHAE | down |
| 201469_s_at | SHC (Src homology 2 domain containing) transforming protein 1 | SHC1 | up |
| 201983_s_at | epidermal growth factor receptor (erythroblastic leukemia viral (v-erb-b) oncogene homolog, avian) | EGFR | down |
| 210671_x_at | mitogen-activated protein kinase 8 | MAPK8 | up |
| 208478_s_at | BCL2-associated X protein | BAX | down |
| 211833_s_at | BCL2-associated X protein | BAX | down |
| 212271_at | mitogen-activated protein kinase 1 | MAPK1 | down |
| 203777_s_at | ribosomal protein S6 kinase, 70kDa, polypeptide 2 | RPS6KB2 | up |

FIG. 6

| | | | |
|---|---|---|---|
| 217575_s_at | Son of sevenless homolog 2 (Drosophila) | SOS2 | up |
| 211551_at | epidermal growth factor receptor (erythroblastic leukemia viral (v-erb-b) oncogene homolog, avian) | EGFR | up |
| 203628_at | insulin-like growth factor 1 receptor | IGF1R | up |
| 209364_at | BCL2-antagonist of cell death | BAD | up |
| 200605_s_at | protein kinase, cAMP-dependent, regulatory, type I, alpha (tissue specific extinguisher 1) | PRKAR1A | up |
| 200638_s_at | tyrosine 3-monooxygenase/tryptophan 5-monooxygenase activation protein, zeta polypeptide | YWHAZ | up |
| 200640_at | tyrosine 3-monooxygenase/tryptophan 5-monooxygenase activation protein, zeta polypeptide | YWHAZ | up |
| 217576_x_at | son of sevenless homolog 2 (Drosophila) | SOS2 | up |
| 201984_s_at | epidermal growth factor receptor (erythroblastic leukemia viral (v-erb-b) oncogene homolog, avian) | EGFR | up |
| 212294_at | guanine nucleotide binding protein (G protein), gamma 12 | GNG12 | up |
| 209296_at | protein phosphatase 1B (formerly 2C), magnesium-dependent, beta isoform | PPM1B | down |
| 203063_at | protein phosphatase 1F (PP2C domain containing) | PPM1F | down |
| 200913_at | protein phosphatase 1G (formerly 2C), magnesium-dependent, gamma isoform | PPM1G | down |
| 213245_at | adenylate cyclase 1 (brain) | ADCY1 | up |
| Cyclophosphamide | P=0.001 | | |
| 202424_at | mitogen-activated protein kinase kinase 2 | MAP2K2 | up |
| 210407_at | protein phosphatase 1A (formerly 2C), magnesium-dependent, alpha isoform | PPM1A | up |
| 218273_s_at | protein phosphatase 2C, magnesium-dependent, catalytic subunit | PPM2C | up |
| 201020_at | tyrosine 3-monooxygenase/tryptophan 5-monooxygenase activation protein, eta polypeptide | YWHAH | up |
| 204906_at | ribosomal protein S6 kinase, 90kDa, polypeptide 2 | RPS6KA2 | up |
| 202801_at | protein kinase, cAMP-dependent, catalytic, alpha | PRKACA | down |

FIG. 6 cont.

| | | | |
|---|---|---|---|
| 203627_at | insulin-like growth factor 1 receptor | IGF1R | up |
| 204524_at | 3-phosphoinositide dependent protein kinase-1 | PDPK1 | down |
| 207005_s_at | B-cell CLL/lymphoma 2 | BCL2 | up |
| 212609_s_at | V-akt murine thymoma viral oncogene homolog 3 (protein kinase B, gamma) | AKT3 | down |
| 202457_s_at | protein phosphatase 3 (formerly 2B), catalytic subunit, alpha isoform | PPP3CA | up |
| 214227_at | Guanine nucleotide binding protein (G protein), gamma 7 | GNG7 | up |
| 210477_x_at | mitogen-activated protein kinase 8 | MAPK8 | down |
| 212312_at | BCL2-like 1 | BCL2L1 | up |
| 213052_at | Protein kinase, cAMP-dependent, regulatory, type II, alpha | PRKAR2A | up |
| 212240_s_at | phosphoinositide-3-kinase, regulatory subunit 1 (p85 alpha) | PIK3R1 | down |
| 217058_at | GNAS complex locus | GNAS | up |
| 214853_s_at | SHC (Src homology 2 domain containing) transforming protein 1 | SHC1 | down |
| Gemcitabine | p=0.001 | | |
| 202741_at | protein kinase, cAMP-dependent, catalytic, beta | PRKACB | up |
| 202742_s_at | protein kinase, cAMP-dependent, catalytic, beta | PRKACB | up |
| 202432_at | protein phosphatase 3 (formerly 2B), catalytic subunit, beta isoform | PPP3CB | up |
| 204686_at | insulin receptor substrate 1 | IRS1 | down |
| 203809_s_at | v-akt murine thymoma viral oncogene homolog 2 | AKT2 | up |
| 207124_s_at | guanine nucleotide binding protein (G protein), beta 5 | GNB5 | down |
| 207157_s_at | guanine nucleotide binding protein (G protein), gamma 5 | GNG5 | down |
| 202429_s_at | protein phosphatase 3 (formerly 2B), catalytic subunit, alpha isoform | PPP3CA | up |
| 203214_x_at | cell division cycle 2, G1 to S and G2 to M | CDC2 | down |
| 206896_s_at | guanine nucleotide binding protein (G protein), gamma 7 | GNG7 | down |
| 208351_s_at | mitogen-activated protein kinase 1 | MAPK1 | up |

FIG. 6 cont.

| | | | |
|---|---|---|---|
| 217620_s_at | phosphoinositide-3-kinase, catalytic, beta polypeptide | PIK3CB | up |
| 212912_at | ribosomal protein S6 kinase, 90kDa, polypeptide 2 | RPS6KA2 | up |
| 204171_at | ribosomal protein S6 kinase, 70kDa, polypeptide 1 /// similar to ribosomal protein S6 kinase, polypeptide 1 | LOC729334 /// LOC731896 /// RPS6KB1 | down |
| 211578_s_at | ribosomal protein S6 kinase, 70kDa, polypeptide 1 | RPS6KB1 | down |
| 202743_at | phosphoinositide-3-kinase, regulatory subunit 3 (p55, gamma) | PIK3R3 | up |
| 219393_s_at | v-akt murine thymoma viral oncogene homolog 3 (protein kinase B, gamma) | AKT3 | up |
| Paclitaxel | p=0.015 | | |
| 203685_at | B-cell CLL/lymphoma 2 | BCL2 | up |
| 200852_x_at | guanine nucleotide binding protein (G protein), beta polypeptide 2 | GNB2 | up |
| 207163_s_at | v-akt murine thymoma viral oncogene homolog 1 | AKT1 | up |
| 207000_s_at | protein phosphatase 3 (formerly 2B), catalytic subunit, gamma isoform | PPP3CC | up |
| 32541_at | protein phosphatase 3 (formerly 2B), catalytic subunit, gamma isoform | PPP3CC | up |
| 215075_s_at | growth factor receptor-bound protein 2 | GRB2 | up |
| 217048_at | --- | --- | up |
| 1861_at | BCL2-antagonist of cell death | BAD | up |
| 209260_at | Stratifin | SFN | up |
| 213699_s_at | tyrosine 3-monooxygenase/tryptophan 5-monooxygenase activation protein, theta polypeptide | YWHAQ | up |
| 222005_s_at | guanine nucleotide binding protein (G protein), gamma 3 | GNG3 | up |
| 200641_s_at | tyrosine 3-monooxygenase/tryptophan 5-monooxygenase activation protein, zeta polypeptide | YWHAZ | up |
| 201375_s_at | protein phosphatase 2 (formerly 2A), catalytic subunit, beta isoform | PPP2CB | up |

FIG. 6 cont.

| Probe Set ID | Gene Title | Gene Symbol | up/down |
|---|---|---|---|
| Breast cancer + Carboplatin | p=0.04 | | |
| 213950_s_at | Protein phosphatase 3 (formerly 2B), catalytic subunit, gamma isoform | PPP3CC | down |
| 208743_s_at | tyrosine 3-monooxygenase/tryptophan 5-monooxygenase activation protein, beta polypeptide | YWHAB | up |
| 203213_at | cell division cycle 2, G1 to S and G2 to M | CDC2 | up |
| 208652_at | protein phosphatase 2 (formerly 2A), catalytic subunit, alpha isoform | PPP2CA | up |
| Breast Cancer + Topotecan | p=0.03 | | |
| 201984_s_at | epidermal growth factor receptor (erythroblastic leukemia viral (v-erb-b) oncogene homolog, avian) | EGFR | up |
| 206047_at | guanine nucleotide binding protein (G protein), beta polypeptide 3 | GNB3 | down |
| 202742_s_at | protein kinase, cAMP-dependent, catalytic, beta | PRKACB | up |
| 209895_at | protein tyrosine phosphatase, non-receptor type 11 (Noonan syndrome 1) | PTPN11 | up |
| 209896_s_at | protein tyrosine phosphatase, non-receptor type 11 (Noonan syndrome 1) | PTPN11 | up |
| 202429_s_at | protein phosphatase 3 (formerly 2B), catalytic subunit, alpha isoform | PPP3CA | up |
| 200641_s_at | tyrosine 3-monooxygenase/tryptophan 5-monooxygenase activation protein, zeta polypeptide | YWHAZ | up |
| Colon cancer + Paclitaxel | p=0.03 | | |
| 214853_s_at | SHC (Src homology 2 domain containing) transforming protein 1 | SHC1 | down |
| 204686_at | insulin receptor substrate 1 | IRS1 | down |
| 203685_at | B-cell CLL/lymphoma 2 | BCL2 | up |
| 219393_s_at | v-akt murine thymoma viral oncogene homolog 3 (protein kinase B, gamma) | AKT3 | down |
| 200746_s_at | guanine nucleotide binding protein (G protein), beta polypeptide 1 | GNB1 | down |

FIG. 7

| Colon cancer + Docetaxel | p=0.03 | | |
|---|---|---|---|
| 214853_s_at | SHC (Src homology 2 domain containing) transforming protein 1 | SHC1 | up |
| 204686_at | insulin receptor substrate 1 | IRS1 | up |
| 203685_at | B-cell CLL/lymphoma 2 | BCL2 | down |
| 219393_s_at | v-akt murine thymoma viral oncogene homolog 3 (protein kinase B, gamma) | AKT3 | up |
| 200746_s_at | guanine nucleotide binding protein (G protein), beta polypeptide 1 | GNB1 | up |
| Ovarian cancer + Carboplatin | p=0.01 | | |
| 217575_s_at | Son of sevenless homolog 2 (Drosophila) | SOS2 | up |
| 211551_at | epidermal growth factor receptor (erythroblastic leukemia viral (v-erb-b) oncogene homolog, avian) | EGFR | up |
| 203628_at | insulin-like growth factor 1 receptor | IGF1R | up |
| 209364_at | BCL2-antagonist of cell death | BAD | up |
| 200605_s_at | protein kinase, cAMP-dependent, regulatory, type I, alpha (tissue specific extinguisher 1) | PRKAR1A | up |
| 200638_s_at | tyrosine 3-monooxygenase/tryptophan 5-monooxygenase activation protein, zeta polypeptide | YWHAZ | up |
| 200640_at | tyrosine 3-monooxygenase/tryptophan 5-monooxygenase activation protein, zeta polypeptide | YWHAZ | up |
| Lung cancer + Cyclophosphamide | p=0.02 | | |
| 201983_s_at | epidermal growth factor receptor (erythroblastic leukemia viral (v-erb-b) oncogene homolog, avian) | EGFR | up |
| 203627_at | insulin-like growth factor 1 receptor | IGF1R | up |
| 203628_at | insulin-like growth factor 1 receptor | IGF1R | up |
| 204524_at | 3-phosphoinositide dependent protein kinase-1 | PDPK1 | down |
| 207005_s_at | B-cell CLL/lymphoma 2 | BCL2 | up |
| 212609_s_at | V-akt murine thymoma viral oncogene homolog 3 (protein kinase B, gamma) | AKT3 | down |

FIG. 7 cont.

| | | | |
|---|---|---|---|
| Melanoma + Paclitaxel | p=0.02 | | |
| 202743_at | phosphoinositide-3-kinase, regulatory subunit 3 (p55, gamma) | PIK3R3 | up |
| 207163_s_at | v-akt murine thymoma viral oncogene homolog 1 | AKT1 | up |
| 209296_at | protein phosphatase 1B (formerly 2C), magnesium-dependent, beta isoform | PPM1B | up |
| 207000_s_at | protein phosphatase 3 (formerly 2B), catalytic subunit, gamma isoform | PPP3CC | up |
| 32541_at | protein phosphatase 3 (formerly 2B), catalytic subunit, gamma isoform | PPP3CC | up |
| 210317_s_at | tyrosine 3-monooxygenase/tryptophan 5-monooxygenase activation protein, epsilon polypeptide | YWHAE | down |
| Leukemia + Carboplatin | p=0.03 | | |
| 201469_s_at | SHC (Src homology 2 domain containing) transforming protein 1 | SHC1 | up |
| 201983_s_at | epidermal growth factor receptor (erythroblastic leukemia viral (v-erb-b) oncogene homolog, avian) | EGFR | down |
| 210671_x_at | mitogen-activated protein kinase 8 | MAPK8 | up |
| 208478_s_at | BCL2-associated X protein | BAX | down |
| 211833_s_at | BCL2-associated X protein | BAX | down |
| 204842_x_at | protein kinase, cAMP-dependent, regulatory, type II, alpha | PRKAR2A | down |
| Leukemia + Gemcitabine | p=0.03 | | |
| 201469_s_at | SHC (Src homology 2 domain containing) transforming protein 1 | SHC1 | up |
| 201983_s_at | epidermal growth factor receptor (erythroblastic leukemia viral (v-erb-b) oncogene homolog, avian) | EGFR | down |
| 210671_x_at | mitogen-activated protein kinase 8 | MAPK8 | up |
| 208478_s_at | BCL2-associated X protein | BAX | down |
| 211833_s_at | BCL2-associated X protein | BAX | down |
| 204842_x_at | protein kinase, cAMP-dependent, regulatory, type II, alpha | PRKAR2A | down |

FIG. 7 cont.

NOSE 7

METHOD OF DIAGNOSING, TREATING AND DETERMINING PROGRESSION AND SURVIVAL OF CANCER CELLS USING BCL-2 ANTAGONIST OF CELL DEATH (BAD) PATHWAY GENE SIGNATURE

CROSS REFERENCE TO RELATED APPLICATIONS

This application is a continuation of International Application No. PCT/US2013/040583 with an international filing date of May 10, 2013, which claims priority to U.S. Provisional Patent Application No. 61/645,369, entitled "The BCL2 Antagonist of Cell Death Apoptosis Pathway Influences Human Cancer Development, Progression and Patient Survival", filed on May 10, 2012, the contents of which are herein incorporated by reference.

STATEMENT OF GOVERNMENT SUPPORT

This invention was made with Government support under Grant No. DAMD17-02-2-0051 awarded by the United States Army Medical Research and Material Command. The Government has certain rights in the invention.

FIELD OF INVENTION

This invention relates to identifying cancerous tissue and treating cancerous tissue. Specifically, the invention discloses a method of diagnosing cancers, methods of treating cancers, methods of determining progression of cancers and methods of determining survival using BAD pathway proteins.

BACKGROUND OF THE INVENTION

Genome-wide approaches to transcriptional and proteomic profiling are promising tools to facilitate individualized care for patients with cancer. As such, biomarkers of therapeutic response and clinical outcome, which inform clinical decision making, will likely become cornerstones of personalized medicine in the future. Currently, the application of such technologies to research provides insights into the biologic basis to cancer development, progression, and response to therapy that were previously not possible.

Recently, using genome-wide expression analysis and a series of functional assays, the BCL-2 antagonist of cell death (BAD) apoptosis pathway and the phosphorylation status of the BAD protein was identified to be associated with the development of ovarian cancer resistance to platinum-based therapy, in vitro and in vivo. (Marchion, et al. BAD phosphorylation determines ovarian cancer chemo-sensitivity and patient survival. Clin Cancer Res. 2011 Oct. 1; 17(19):6356-66). Furthermore, the expression of the BAD pathway is associated with overall survival for patients with ovarian cancer. BCL-2 family proteins are key regulators of apoptosis. Pro-apoptotic BAX and BAK drive cell death by increasing mitochondrial outer membrane permeability, resulting in cytochrome c release, cytoplasmic caspase activation, and, ultimately, cell death. Anti-apoptotic proteins such as BCL-2, BCL-xL, and BCL-W promote survival by binding and inhibiting BAX and BAK. A third group of BCL-2 family members, which includes BAD, BID, BIM, NOXA, and PUMA, promote apoptosis by directly binding and inhibiting the anti-apoptotic BCL-2 proteins. (Youle and Strasser, The BCL-2 protein family: opposing activities that mediate cell death. Nat Rev Mol Cell Biol 2008; 9: 47-59; Danial, BAD: undertaker by night, candyman by day. Oncogene 2008; 27 Suppl 1: S53-70) It is believed the phosphorylation status of BAD influences its ability to bind BCL and BCL-xL, levels of unbound of BAX, and hence mitochondrial membrane permeability and apoptosis.

What is needed is a method of diagnosing, treating, determining survival, and monitoring progression of cancers using BAD pathway proteins.

SUMMARY OF INVENTION

In light of the pivotal role that the BCL-2 proteins play in cellular apoptosis and recent findings suggesting that BAD phosphorylation influences cancer chemo-sensitivity and clinical outcome, the role of the BAD pathway in the development, progression, and overall survival was characterized from a broad range of human cancers. Furthermore, associations between expression of the pathway and the sensitivity of an array of different human cancer cell types to a spectrum of different cytotoxic drugs were evaluated. The pathway was also explored as a potential therapeutic target.

A Principle Component Analysis (PCA) score (Jolliffe, Principal Component Analysis. 2 ed. New York: Springer; 2002) was utilized to quantify overall expression of the BAD pathway in genomic data from 1,254 patient samples in 11 independent datasets that included normal tissue and corresponding pre-invasive and invasive cancer specimens. Associations were explored between BAD pathway expression and 1) clinical outcome for patients with cancer and 2) sensitivity of 59 human cancer cell lines to a range of cytotoxic chemotherapeutic agents. The influence of BAD protein phosphorylation on in vitro chemo-sensitivity was evaluated in a series of cancer cell lines.

In an embodiment, a method of diagnosing cancer is presented comprising: obtaining an expression level of at least one Bcl-2 antagonist of cell death (BAD) pathway gene in a sample suspected of being cancerous or pre-cancerous; using the expression level of the at least one Bcl-2 antagonist of cell death (BAD) pathway gene to obtain a BAD Pathway Gene Expression Signature (BPGES) score of the sample using Principal Component Analysis (PCA); obtaining an expression level of a control; using the expression level of the control to obtain a BAD Pathway Gene Expression Signature (BPGES) score of the control; and comparing the BPGES score of the sample suspected of being cancerous or pre-cancerous to the BPGES score of the control sample. A lower BAD Pathway Gene Expression Signature (BPGES) score for the sample suspected of being cancerous or pre-cancerous as compared to the control sample is indicative of cancer. The cancer may be selected from the group consisting of breast cancer, ovarian cancer, endometrial cancer, colon cancer, lung cancer, leukemia, brain cancer and melanoma.

The at least one BAD pathway gene may be selected from the group consisting of those genes listed in FIGS. 6 and 7.

The cancer being diagnosed may be pre-cancerous tissue, pre-invasive cancerous tissue, or invasive cancerous tissue.

In another embodiment, a method of determining survival from cancer is presented comprising: identifying at least one BAD pathway gene differentially expressed in cells sensitive to at least one chemotherapeutic versus cells resistant to the at least one chemotherapeutic and comparing the least one BAD pathway gene in a sample suspected of being cancerous or pre-cancerous to a control sample. A lower differential expression of the at least one BAD pathway gene of the sample suspected of being cancerous or pre-cancerous as compared to the control sample may be indicative of cancer non-survival.

The cancer may be selected from the group consisting of breast cancer, ovarian cancer, endometrial cancer, colon cancer, lung cancer, leukemia, brain cancer and melanoma.

The chemotherapeutic may be carboplatin, cyclophosphamide, topotecan, docetaxel, paclitaxel, or gemcitabine.

The at least one BAD pathway gene may be selected from the group consisting of genes listed in FIGS. 6 and 7.

In a further embodiment, a method of identifying cancer sensitivity to chemotherapeutics is presented comprising: obtaining a BAD Pathway Gene Expression Signature (BPGES) score of a sample suspected of being cancerous or pre-cancerous and comparing the BAD Pathway Gene Expression Signature (BPGES) score of the sample suspected of being cancerous or pre-cancerous to a control sample. The BAD Pathway Gene Expression Signature (BPGES) score identifies the chemosensitivity of cancerous or pre-cancerous cells to at least one chemotherapeutic and a low BAD Pathway Gene Expression Signature (BPGES) score may be indicative of chemoresistant cancer.

The chemotherapeutic may be carboplatin, topotecan, docetaxel, gemcitabine and paclitaxel.

The BAD Pathway Gene Expression Signature (BPGES) score may be determined by obtaining an expression level of at least one BAD pathway gene selected from the group consisting of genes listed in FIGS. 6 and 7 and applying Principal Component Analysis (PCA).

In another embodiment, a method of treating cancer is presented comprising administering a therapeutically effective amount of an agent that targets the Bcl-2 antagonist of cell death (BAD) pathway. The cancer may be selected from the group consisting of breast cancer, ovarian cancer, endometrial cancer, colon cancer, lung cancer, leukemia, brain cancer and melanoma. The agent may modulate phosphorylation of BAD protein. The agent may reduce the level of active CDK1 or increase the level of PP2C.

In a further embodiment, a method of monitoring neoplasia progression from one biological state to another in a tumor sample is presented comprising: obtaining a first BAD Pathway Gene Expression Signature (BPGES) score from a tumor sample at a first timepoint; obtaining a second BPGES score from the tumor sample at a second timepoint wherein the second timepoint is at a given interval after the first timepoint; and comparing the first and the second BPGES score to each other. A decrease in the second BPGES score as compared to the first BPGES score may be indicative of neoplasia progression and an increase in the second BPGES score as compared to the first BPGES score is indicative of neoplasia regression. The neoplasia may be selected from the group consisting of breast cancer, ovarian cancer, endometrial cancer, colon cancer, lung cancer, leukemia, brain cancer and melanoma.

The BAD Pathway Gene Expression Signature (BPGES) score may be determined by obtaining an expression level of at least one BAD pathway gene selected from the group consisting of genes listed in FIGS. 6 and 7 and applying Principal Component Analysis (PCA).

The neoplasia progression being monitored may be normal tissue to pre-cancerous tissue, normal to pre-invasive cancerous tissue, pre-cancerous tissue to pre-invasive cancerous tissue, or pre-invasive cancerous tissue to invasive cancerous tissue.

BRIEF DESCRIPTION OF THE DRAWINGS

For a fuller understanding of the invention, reference should be made to the following detailed description, taken in connection with the accompanying drawings, in which:

FIG. 6 is a table listing BAD pathway genes differentially expressed in all NCI60 cancer cell types by drug.

FIG. 7 is a table listing BAD pathway genes differentially expressed by NCI60 cancer cell types and by drug.

DETAILED DESCRIPTION OF THE PREFERRED EMBODIMENT

Figure 1A:
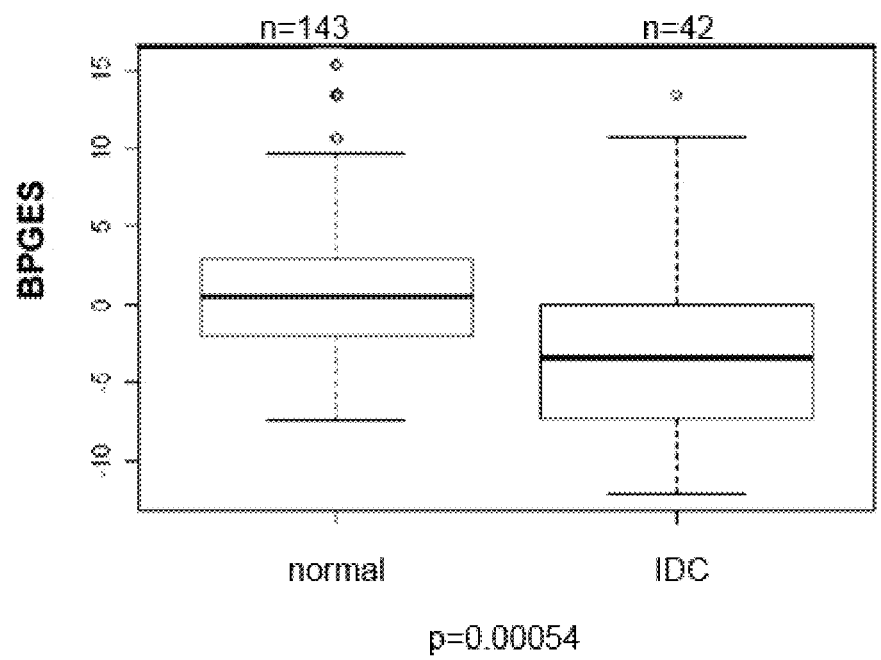
FIG. 1A-F is a series of images depicting the BAD pathway gene expression signature (BPGES) score is associated with cancer development and progression. The mean BPGES score was associated with the development of cancer (normal tissue, pre-invasive tissue, pre-invasive, then invasive cancer) in all tissue types evaluated, including (A) breast samples; (B) colon samples; (C) lung samples; (D) breast samples; (E) Endometrial samples; (F) ovarian endometrioses. IDC=invasive ductal carcinoma, ADH=atypical ductal hyperplasia, DCIS=ductal carcinoma in situ, AEH=atypical endometrial hyperplasia, CA=cancer.
Figure 1B:
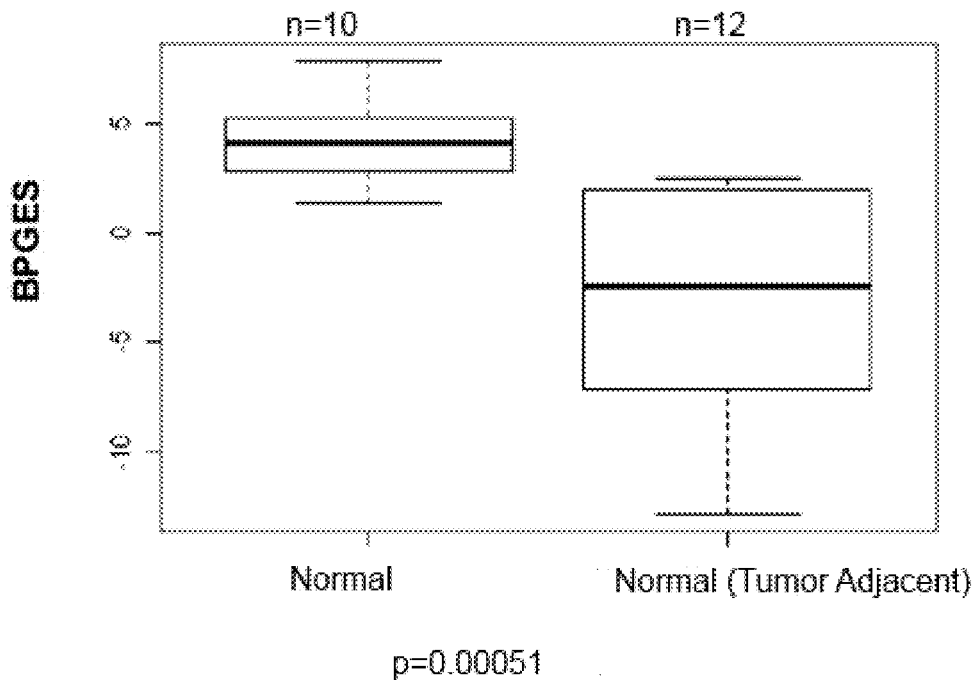
Figure 1C:
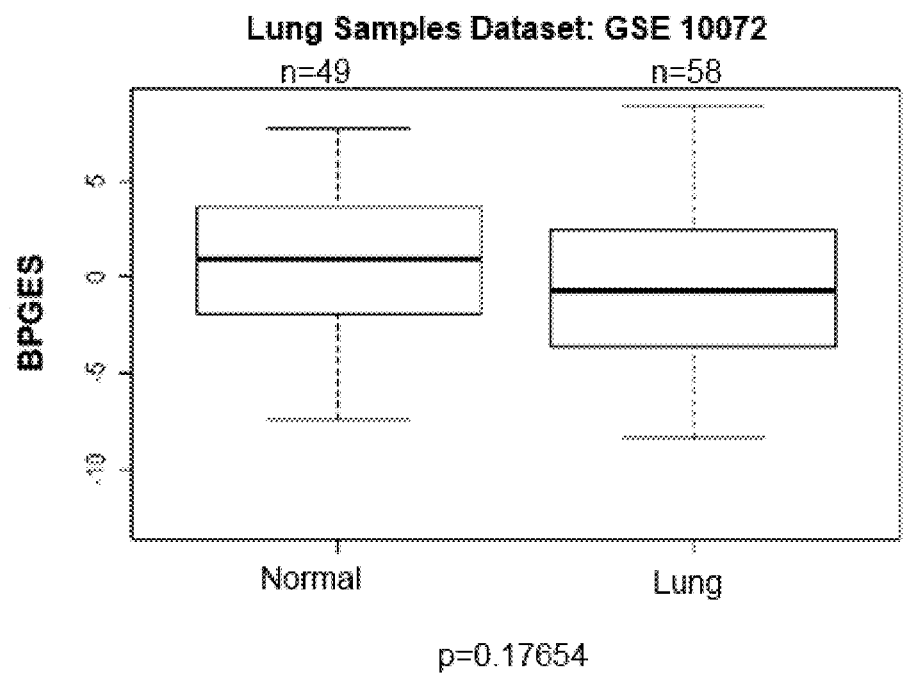
Figure 1D:
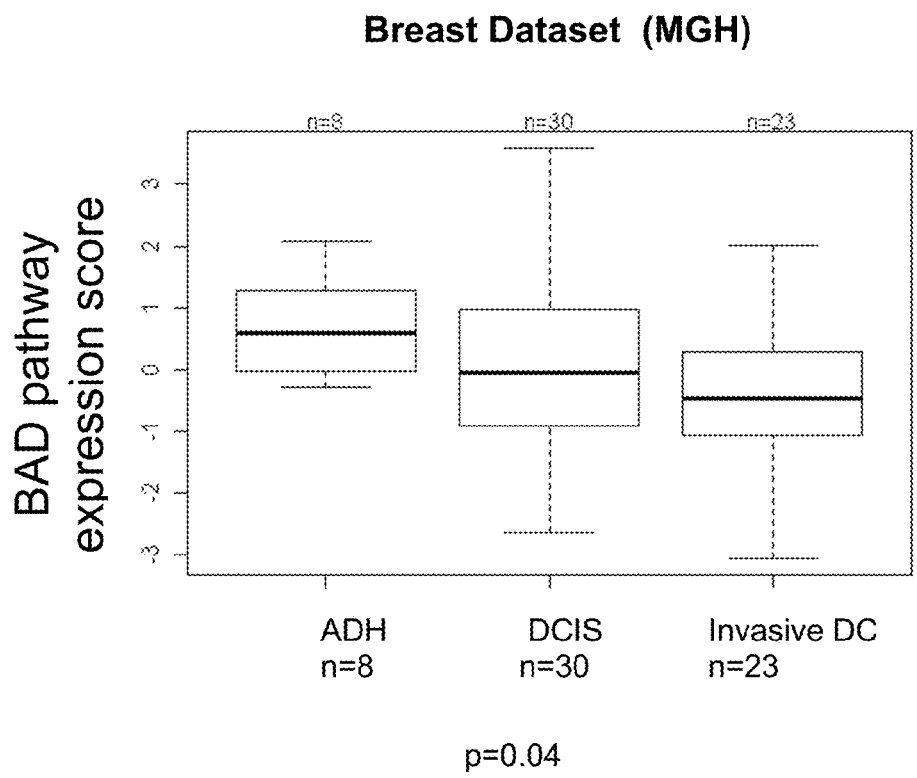

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Definitions

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

The term "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose, such as a pharmaceutical formulation. For example, "about" can mean within 1 or more than 1 standard deviation, per the practice in the art. Alternatively, "about" can mean a range of up to 20%, preferably up to 10%, more preferably up to 5% and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range, to the tenth of the unit. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

The term "agent" as used herein describes a composition, compound, chemical or extract that can be administered or tested by the present invention as a modulator of a BAD pathway gene. The chemical can be of any composition such as inorganic, organic, or a biomolecule. A biomolecule can be a molecule of any biological origin that can be found in or produced by, at least in part, a cell. This definition includes, but is not limited to, polypeptides, lipids, nucleic acids, carbohydrates and combinations thereof "Agent" is used interchangeably herein with "compound", "composition", "chemical", "drug", and "extract".

"Subject" is used to describe an animal, preferably a mammal, more preferably a human, to whom treatment is administered, including prophylactic treatment with the compositions of the present invention. "Subject" and "patient" are used interchangeably herein.

The genes of the present invention may serve as biomarkers for: (1) the diagnosis of disease; (2) the prognosis of diseases (e.g. monitoring disease progression or regression from one biological state to another); (3) the susceptibility or prediction of response to treatment for a disease; or (4) the evaluation of the efficacy to a treatment for disease. For the diagnosis of disease, the level of the specific gene in the subject can be compared to a baseline or control level in which if the level is above the control level, a certain disease is implicated. The prognosis of disease can be assessed by comparing the level of the specific gene biomarker at a first timepoint to the level of the biomarker at a second timepoint which occurs at a given interval after the first timepoint. The prediction of response to treatment for a disease can be determined by obtaining the level of a specific gene biomarker and correlating this level to an overall BAD pathway gene signature score. The evaluation of the efficacy of the treatment for a disease can be assessed by comparing the level of the specific gene biomarker at a first timepoint before administration of the treatment to the level of the biomarker at a second timepoint which occurs at a specified interval after the administration of the treatment.

The term "expression level" as used herein refers to detecting the amount or level of expression of a biomarker of the present invention. The act of actually detecting the expression level of a biomarker refers to the act of actively determining whether a biomarker is expressed in a sample or not. This act can include determining whether the biomarker expression is upregulated, downregulated or substantially unchanged as compared to a control level expressed in a sample. The expression level in some cases may refer to detecting transcription of the gene encoding a biomarker protein and/or to detecting translation of the biomarker protein.

Expression of genes/transcripts and/or polypeptides encoded by the genes represented by the biomarkers of the present invention can be measured by any of a variety of methods known in the art. In general, expression of a nucleic acid molecule (e.g. RNA or DNA) can be detected by any suitable method or technique of measuring or detecting gene or polynucleotide sequence or expression. Such methods include, but are not limited to, polymerase chain reaction (PCR), reverse transcriptase PCR (RT-PCR), in situ PCR, quantitative PCR (q-PCR), in situ hybridization, Southern blot, Northern blot, sequence analysis, microarray analysis, detection of a reporter gene, or any other DNA/RNA hybridization platforms.

The term "quantifying" or "quantitating" when used in the context of quantifying transcription levels of a gene can refer to absolute or relative quantification. Absolute quantification can be achieved by including known concentration(s) of one or more target nucleic acids and referencing the hybridization intensity of unknowns with the known target nucleic acids (e.g. through the generation of a standard curve). Alternatively, relative quantification can be achieved by comparison of hybridization signals between two or more genes, or between two or more treatments to quantify the changes in hybridization intensity and, by implication transcription level.

Methods to measure protein/polypeptide expression levels of selected biomarkers in the present invention include, but are not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, liquid chromatography mass spectrometry (LC-MS), matrix-assisted laser desorption/ionization time-of-flight (MALDI-TOF), mass spectrometry, microcytometry, microarray, microscopy, fluorescence activated cell sorting (FACS), flow cytometry, and assays based on a property of the protein including but not limited to DNA binding, ligand binding, or interaction with other protein partners.

The terms "diagnosing" or "diagnosis" as used herein refers to the determination of whether a subject comprises a disease or condition such as cancer. "Diagnosing" can also refer to distinguishing one cancer from another.

The term "prognosis" refers to the determination or prediction of the course of disease or condition or to monitoring disease progression or regression from one biological state to another. Prognosis can include the determination of the time course of a disease, with or without treatment. Where treatment is included, the prognosis includes determining the efficacy of the treatment for the disease or condition.

The terms "risk or susceptibility" as used herein refers to the determination as to whether a subject would or would not respond to a particular therapy such as chemotherapy, such as one or more alkylating agents; radiotherapy; adjuvant therapy; surgery; or a combination thereof in order to optimize therapy for an individual subject. Cancers that express biomarkers that are indicative of a more highly aggressive cancer or poor prognosis may be treated with more aggressive therapies.

The term "treatment" or "treating" as used herein refers to the ability to ameliorate, suppress, mitigate, or eliminate the clinical symptoms after the onset of a disease state. Treatment can include chemicals, such as chemotherapeutic agents or test compounds, and/or non-chemical treatment such as radiation, electrical pulses, and magnetic fields. An effective or successful treatment provides a clinically observable improvement.

The term "biomarker" is used herein to refer to a molecule whose level of nucleic acid or protein product has a quantitatively differential concentration or level with respect to an aspect of a biological state of a subject. "Biomarker" is used interchangeably with "marker" herein. The level of the biomarker can be measured at both the nucleic acid level as well as the polypeptide level. At the nucleic acid level, a nucleic acid gene or a transcript which is transcribed from any part of the subject's chromosomal and extrachromosomal genome, including for example the mitochondrial genome, may be measured. Preferably an RNA transcript, more preferably an RNA transcript includes a primary transcript, a spliced transcript, an alternatively spliced transcript, or an mRNA of the biomarker is measured. At the polypeptide level, a pre-propeptide, a propeptide, a mature peptide or a secreted peptide of the biomarker may be measured. A biomarker can be used either solely or in conjunction with one or more other identified biomarkers so as to allow correlation to the biological state of interest as defined herein. Specific examples of biomarkers covered by the present invention include genes involved in cell cycle regulation, apoptosis, cell proliferation, and angiogenesis. More specifically, biomarkers of the present invention include those genes and proteins associated with the Bcl-2 antagonist of cell death apoptosis pathway (BAD).

The term "biological state" as used herein refers to the result of the occurrence of a series of biological processes. As the biological processes change relative to each other, the biological state also changes. One measurement of a biological state is the level of activity of biological variables such as biomarkers, parameters, and/or processes at a specified time or under specified experimental or environmental conditions. A biological state can include, for example, the state of an individual cell, a tissue, an organ, and/or a multicellular organism. A biological state can be measured in samples taken from a normal subject or a diseased subject thus measuring the biological state at different time intervals may indicate the progression of a disease in a subject. The biological state may include a state that is indicative of disease (e.g. diagnosis); a state that is indicative of the progression or regression of the disease (e.g. prognosis); a state that is indicative of the susceptibility (risk) of a subject to therapy for the disease; and a state that is indicative of the efficacy of a treatment of the disease. The biological state may include normal cells or tissues, pre-cancerous cells or tissues, pre-invasive cells or tissues and invasive cells or tissue.

The term "cell" or "cells" is used synonymously herein and refers to in vitro cultures of mammalian cells grown and maintained as known in the art, as well as biological samples obtained from tumor specimens or normal specimens in vivo.

A "BAD pathway gene" as used herein refers to a gene which when modulated (either induced or repressed) affects the BAD pathway. Specific BAD pathway genes utilized in the present invention include, but are not limited to, those genes listed in FIGS. 6 and 7.

The terms "BAD Pathway Gene Expression Signature Score" (BPGES) as used herein refers to a number generated using the first principal component of principal component analysis to reflect the overall expression profile for the BAD pathway. This number is a summation of the BAD pathway genes and is based on the assigned weights of each gene. The BPGES is based on a weighted value that is generated using principal component analysis according to the methodology described in Chen D. T. et al. and Marchion et al., both of which are incorporated herein in its entirety by reference. (Chen D. T. et al., Proliferative genes dominate malignancy-risk gene signature in histologically-normal breast tissue. Breast Cancer Res Treat. 2010 January; 119(2):335-46; see also, Marchion et al., BAD phosphorylation determines ovarian cancer chemo-sensitivity and patient survival. Clin Cancer Res 2011 Oct. 1, 17(19):6356-66) It is known that directional signs of PCA scores are recognized to be arbitrary and can vary between software and algorithm used to calculate the PCA model (Jolliffe, Principal Component Analysis. 2 ed. New York: Springer; 2002). However, this does not affect the interpretation of the PCA model and can be easily solved by multiplying both scores and loadings by −1, a 180° rotation. Reflecting this, and for the sake of consistency, analyses of the PCA model were rotated so a high score corresponded to a normal sample or to an increased survival time.

The terms "BAD Pathway Gene Expression Signature" as used herein refers to the specific pattern of gene modulation of BAD pathway genes in neoplasias, specifically in breast, colon, lung, endometrium, ovarian and brain cancers. This BAD pathway gene signature is comprised of genes associated with the BAD pathway including, but not limited to, the genes listed in FIGS. 6 and 7.

The term "sample" as used herein refers to any physical sample that includes a cell or a cell extract from a cell, a tissue, or an organ including a biopsy sample. The sample can be from a biological source such as a subject or animal, or a portion thereof, or can be from a cell culture. Samples from a biological source can be from a normal or an abnormal organism, such as an organism known to be suffering from a condition or a disease state such as a neoplasm, or any portion thereof. Samples can also be from any fluid, tissue or organ including normal and abnormal (diseased or neoplastic) fluid, tissue or organ. Samples from a subject or animal can be used in the present invention as obtained by the subject or animal and processed or cultured such that cells from the sample can be sustained in vitro as a primary or continuous cell culture or cell line. A "tumor sample" is a sample that includes at least one cell derived from at least one tumor.

A "therapeutically effective amount" as used herein is defined as concentrations or amounts of components which are sufficient to effect beneficial or desired clinical results, including, but not limited to, inhibiting neoplastic transformation of cells; inhibiting inappropriate cell growth; inhibiting the proliferation of neoplastic/cancerous cells; inducing apoptosis in neoplastic/cancerous cells; and enhancing the therapeutic effect of chemotherapy medications. Compositions of the present invention can be used to effect a favorable change in the condition whether that change is an improvement or a complete elimination of symptoms due to neoplasia/cancer. In accordance with the present invention, a suitable single dose size is a dose that is capable of preventing or alleviating (reducing or eliminating) a symptom in a subject when administered one or more times over a suitable time period. One of skill in the art can readily determine appropriate single dose sizes for systemic administration based on the size of the animal and the route of administration. The therapeutically effective amount of the compositions of the present invention encompasses providing cancer treatment or enhancing cancer treatment without causing significant side effects or adverse reactions.

The term "baseline level" or "control level" of biomarker expression or activity refers to the level against which biomarker expression in the test sample can be compared. In some embodiments, the baseline level can be a normal level, meaning the level in a sample from a normal patient. This allows a determination based on the baseline level of biomarker expression or biological activity, whether a sample to be evaluated for disease cell growth has a measurable increase, decrease, or substantially no change in biomarker expression as compared to the baseline level. The term "negative control" used in reference to a baseline level of biomarker expression generally refers to a baseline level established in a sample from the subject or from a population of individuals which is believed to be normal (e.g. non-tumorous, not undergoing neoplastic transformation, not exhibiting inappropriate cell growth). In other embodiments, the baseline level can be indicative of a positive diagnosis of disease (e.g. positive control). The term "positive control" as used herein refers to a level of biomarker expression or biological activity established in a sample from a subject, from another individual, or from a population of individuals, where the sample was believed, based on data from that sample, to have the disease (e.g. tumorous, cancerous, exhibiting inappropriate cell growth). In other embodiments, the baseline level can be established from a previous sample from the subject being tested, so that the disease progression or regression of the subject can be monitored over time and/or the efficacy of treatment can be evaluated.

The term "neoplasia", "cancer", "tumor", "cancerous", and malignant" as used herein, refer to the physiological condition in mammals that is typically characterized by unregulated cell growth or the presence of tumors. The terms are used interchangeably herein. Examples of cancer benefited by the present invention include, but are not limited to, brain cancer including gliomas, breast cancer, ovarian cancer, endometrial cancer, lung cancer including non-small cell lung cancer, skin cancer including melanoma, renal cancer and colon cancer.

The term "pre-cancerous" as used herein refers to a physiological condition in mammals that is typically associated with a significantly increased risk of cancer.

The term "pre-invasive" as used herein refers to a physiological condition in mammals that is typically associated with a localized tumor or cancer that has a risk of spreading to other tissues of the body.

The term "invasive" as used herein refers to a physiological condition in mammals that is typically associated with cancer which has spread to multiple locations or tissues in the body.

The term "gene expression product" or "expression product" as used herein refers to an RNA transcribed from a gene (either pre- or post-processing) or an amino acid (e.g. a polypeptide, protein, or peptide regardless of any secondary modifications, such as glycosylation, lipidation or phosphorylation) encoded by the gene and generated by the gene when the gene is transcribed (either pre- or post-modification) and translated. An agent is said to increase gene expression if the application of a therapeutically effective amount of the agent to a cell or subject results in an increase in either an RNA or polypeptide expression product or both. An agent is said to decrease gene expression if the application of a therapeutically effective amount of the agent to a cell or subject results in a decrease in either an RNA or polypeptide expression product or both.

The term "polynucleotide" as used herein refers to a polymeric molecule that has a backbone that supports bases capable of hydrogen bonding to typical polynucleotides. The polymer backbone presents the bases in a manner that is effective to allow such hydrogen bonding in a sequence specific fashion between the polymeric molecule and a typical polynucleotide, such as single-stranded DNA. Polymeric molecules include both single and double stranded DNA or RNA and can include polymers having backbone modifications. It includes the recited sequences as well as their complementary sequences, which can be easily ascertained by those of ordinary skill in the art.

The term "nucleic acid" as used herein may be double-stranded, single-stranded, or contain portions of both double and single stranded sequence. If the nucleic acid is single-stranded, the sequence of the other strand is also identifiable and thus the definition includes the complement of the sequence disclosed.

The term "polypeptide" as used herein refers to a compound made up of a single-chain of amino acid residues that are linked by peptide bonds. The term "protein" may be synonymous with the term "polypeptide" or may refer, in addition, to a complex of two or more polypeptides. Generally, polypeptides and proteins are formed predominantly of naturally occurring amino acids.

An "isolated polynucleotide" as used herein refers to a polynucleotide which is separated from other nucleic acid molecules which are present in the natural source of the polynucleotide. Preferably, an "isolated polynucleotide" is free of sequences which naturally flank the polynucleotide in the genomic DNA of the organism from which the nucleic acid is derived. An "isolated polynucleotide" is substantially free of other cellular material, gel materials, and culture medium when produced by recombinant techniques, or substantially free of chemical precursors or other chemicals when chemically synthesized. The polynucleotides of the present invention may be isolated from a variety of sources, such as PCR amplification from genomic DNA, mRNA, or cDNA libraries derived from the mRNA using standard techniques.

A "probe set" as used herein refers to a group of one or more polynucleotides that each selectively hybridize to the same target (for example, a specific genomic region or mRNA) that correlates with cancer diagnosis. As such, a single "probe set" may comprise any number of different isolated polynucleotides that selectively hybridize to a given target. A "probe" is a singular polynucleotide that selectively hybridizes to a target.

Evasion of apoptotic signaling is a hallmark of cancer cells (Hanahan and Weinberg, Hallmarks of cancer: the next generation. Cell; 144: 646-74). Because BCL-2 family proteins are critical determinants of cellular apoptosis and survival, the role of the BAD apoptosis pathway was evaluated as a determinant of cancer development in a series of cancer types. A numeric PCA score (termed BPGES) was developed, which represents a summary measure of activity for the entire BAD apoptosis pathway, and analyzed a series of clinico-genomic datasets for representation of this summary measure of pathway activity. Analyses revealed differences in BAD pathway expression between normal and cancer human tissue samples (including breast, colon, and endometrium). Moreover, a correlation was found between BPGES and the transition of normal tissues to pre-cancerous/pre-invasive and on to invasive disease. These results suggest that BPGES changes with transition from normal tissues to pre-invasive and to invasive carcinoma and is related to pBAD (serine-155) protein levels in breast, brain, melanoma, and lung cancer cell lines. Furthermore, depletion of a BAD protein kinase and phosphatase in cancer cell lines decreases and increases, respectively, levels of pBAD with parallel changes in cellular proliferation rates consistent with the paradigm that pBAD has a pro-survival function. A correlation was demonstrated between resistance to cytotoxic agents and BAD phosphorylation, a finding that has important implications for chemotherapeutic approaches to cancer treatment. In light of these findings, the influence of BAD pathway activity was evaluated on overall survival in patients with ovarian, colon, breast, and brain cancer. An association between BPGES (which is associated with low pBAD protein levels in vitro) and overall survival for all cancer types analyzed was identified. In summary, these data appear to suggest that the BAD pathway is involved in cancer development, progression, response to therapy, and overall survival and that these effects may be due to changes in the phosphorylation status of the BAD protein. The influence of the BAD pathway and phospho-protein appear to apply to a broad range of human cancer types and also to sensitivity of these cancers to a broad range of cytotoxic drugs.

The cellular function of BCL2 proteins in determining cell survival reflects complex interactions that include differential expression and post-translational modifications. Heterodimerization between BAD and BCL-2, BCL-xL, or BCL-W promotes apoptosis by displacement of BAK and BAX. (Yang, et al., Bad, a heterodimeric partner for Bcl-XL and Bcl-2, displaces Bax and promotes cell death. Cell 1995; 80: 285-91; Holmgreen, et al., Survival activity of Bcl-2 homologs Bcl-w and A1 only partially correlates with their ability to bind pro-apoptotic family members. Cell Death Differ 1999; 6: 525-32; Zha, et al., Serine phosphorylation of death agonist BAD in response to survival factor results in binding to 14-3-3 not BCL-X(L). Cell 1996; 87: 619-28; Jia, et al., Subcellular distribution and redistribution of Bcl-2 family proteins in human leukemia cells undergoing apoptosis. Blood 1999; 93: 2353-9; Datta, et al., 14-3-3 proteins and survival kinases cooperate to inactivate BAD by BH3 domain phosphorylation. Mol Cell 2000; 6: 41-51; Roy, et al., Bad targets the permeability transition pore independent of Bax or Bak to switch between Ca2+-dependent cell survival and death. Mol Cell 2009; 33: 377-88). The pro-apoptotic activity of BAD is inhibited by phosphorylation of serine-112, -136, and -155. Phosphorylation of these residues is required to prevent BAD-induced apoptosis. (Datta, et al., 14-3-3 proteins and survival kinases cooperate to inactivate BAD by BH3 domain phosphorylation. Mol Cell 2000; 6: 41-51; Tan, et al., BAD Ser-155 phosphorylation regulates BAD/Bcl-XL interaction and cell survival. J Biol Chem 2000; 275: 25865-9). Serine-112 and -136 phosphorylation promotes an interaction with the phosphor-serine binding protein 14-3-3, which sequesters BAD in the cytosol. (Zha, et al., Serine phosphorylation of death agonist BAD in response to survival factor results in binding to 14-3-3 not BCL-X(L). Cell 1996; 87: 619-28). Protein 14-3-3 binding also makes the serine-155 site more accessible to survival-promoting kinases, which phosphorylate this site within the BH3 domain and consequently inhibit the interaction between BAD and its anti-apoptotic partners. (Datta, et al., 14-3-3 proteins and survival kinases cooperate to inactivate BAD by BH3 domain phosphorylation. Mol Cell 2000; 6: 41-51; Tan, et al., BAD Ser-155 phosphorylation regulates BAD/Bcl-XL interaction and cell survival. J Biol Chem 2000; 275: 25865-9; Zhou, et al., Growth factors inactivate the cell death promoter BAD by phosphorylation of its BH3 domain on Ser155. J Biol Chem 2000; 275: 25046-51). Because post-translational modifications of BAD represent a key control point between cell survival and apoptosis, BAD phosphorylation is frequently deregulated in cancer. Activation of multiple signaling pathways, such as AKT and PKA, by growth factors, cytokines, or oncogenic mutations can contribute to increased BAD phosphorylation on the inhibitory serine residues. (Danial, BAD: undertaker by night, candyman by day. Oncogene 2008; 27 Suppl 1: S53-70). In contrast, phosphatase activity by PP2C results in BAD activation via removal of the phosphate group from serine-155, restoring the ability of BAD to bind BCL-2, BCL-xL, and BCL-W. (Tan, et al., BAD Ser-155 phosphorylation regulates BAD/Bcl-XL interaction and cell survival. J Biol Chem 2000; 275: 25865-9).

Several mitogenic signaling pathways converge on BAD to suppress apoptosis, such as the PI3K/AKT and cAMP/PKA pathways. AKT and PKA activity was observed to increase in cancer cells compared to their normal counterparts. AKT is an effector kinase in the phosphoinositide 3-kinase (PI3K) pathway, which is activated in response to extracellular growth stimuli and receptor tyrosine kinase signaling. (Engelman, Targeting PI3K signaling in cancer: opportunities, challenges and limitations. Nat Rev Cancer 2009; 9: 550-62). AKT phosphorylates BAD on serine-136, which promotes 14-3-3 binding and cytosolic sequestration. (Zha, et al., Serine phosphorylation of death agonist BAD in response to survival factor results in binding to 14-3-3 not BCL-X(L). Cell 1996; 87: 619-28;

Datta, et al., Akt phosphorylation of BAD couples survival signals to the cell-intrinsic death machinery. Cell 1997; 91: 231-41; del Peso, et al., Interleukin-3-induced phosphorylation of BAD through the protein kinase Akt. Science 1997; 278: 687-9). The tumor suppressor PTEN (phosphatase and tensin homolog) opposes PI3K signaling by dephosphorylating the lipids required for AKT activation and is one of the most frequently mutated tumor suppressors in human cancers. Oncogenic mutations also occur both in PI3K subunits and in AKT itself. (Engelman, Targeting PI3K signaling in cancer: opportunities, challenges and limitations. Nat Rev Cancer 2009; 9: 550-62). Each of these mutations results in constitutive activation of AKT, which blocks BAD-induced apoptosis. (Datta, et al., Akt phosphorylation of BAD couples survival signals to the cell-intrinsic death machinery. Cell 1997; 91: 231-41; Blume-Jensen, et al., The kit receptor promotes cell survival via activation of PI 3-kinase and subsequent Akt-mediated phosphorylation of Bad on Ser136. Curr Biol 1998; 8: 779-82). PKA consists of two regulatory and two catalytic subunits. Upon activation of G-protein coupled receptors by extracellular stimuli, such as cytokines and hormones, adenylate cyclase catalyzes the conversion of ATP to cAMP, which binds the regulatory subunits of PKA. The catalytic subunits are then released, phosphorylating multiple substrates, including BAD on both serine-112 and serine-155. (Harada, et al., Phosphorylation and inactivation of BAD by mitochondria-anchored protein kinase A. Mol Cell 1999; 3: 413-22; Lizcano, et al., Regulation of BAD by cAMP-dependent protein kinase is mediated via phosphorylation of a novel site, Ser155. Biochem J 2000; 349: 547-57; Virdee, et al., Phosphorylation of the pro-apoptotic protein BAD on serine 155, a novel site, contributes to cell survival. Curr Biol 2000; 10: R883). Constitutive activation of PKA via an inactivating mutation in PRKAR1A, a gene encoding one of the regulatory subunits, causes decreased apoptosis and increased proliferation and underlies a familial cancer predisposition syndrome. (Robinson-White, et al., PRKAR1A inactivation leads to increased proliferation and decreased apoptosis in human B lymphocytes. Cancer Res 2006; 66: 10603-12; Kirschner, et al., Mutations of the gene encoding the protein kinase A type I-alpha regulatory subunit in patients with the Carney complex. Nat Genet 2000; 26: 89-92).

Phosphatase activity can also directly result in BAD activation. Serine/threonine protein phosphatase 2C (PP2C) dephosphorylates BAD at serine-155. (Klumpp, et al., Protein phosphatase type 2C dephosphorylates BAD. Neurochem Int 2003; 42: 555-60). Removal of the phosphate group from serine-155 restores the ability of BAD to bind BCL-2, BCL-xL, and BCL-W. (Tan, et al., BAD Ser-155 phosphorylation regulates BAD/Bcl-XL interaction and cell survival. J Biol Chem 2000; 275: 25865-9). PP2C has been shown to possess tumor suppressor activity. (Lammers and Lavi, Role of type 2C protein phosphatases in growth regulation and in cellular stress signaling. Crit Rev Biochem Mol Biol 2007; 42: 437-61). Consistent with these findings, many cancer cell lines exhibit decreased PP2C expression (data not shown). Furthermore, PP2C knockdown promotes cancer cell growth, suggesting that the role of PP2C in promoting BAD-dependent apoptosis may be critical for tumor suppression.

Increased levels of CDK1 were also observed in cancer cell lines. Previous studies have shown that BAD activity is promoted by CDK1-dependent phosphorylation of serine-128, which counteracts the inhibitory serine-136 phosphorylation mark blocking the interaction between pBAD and 14-3-3. (Konishi, et al., Cdc2 phosphorylation of BAD links the cell cycle to the cell death machinery. Mol Cell 2002; 9: 1005-16). However, data suggest that silencing CDK1 expression does not prevent apoptosis in the tumor cell lines tested, but leads to increased cell death. This is likely attributable to the primary role of CDK1 in cell cycle progression. CDK1-dependent phosphorylation of BAD may be required only as a failsafe mechanism for apoptosis in the event of aberrant mitosis, which is supported by the recent finding that cyclin B-CDK1 phosphorylation of anti-apoptotic BCL-2 family members marks them for proteasomal degradation. (Harley, et al., Phosphorylation of Mcl-1 by CDK1-cyclin B1 initiates its Cdc20-dependent destruction during mitotic arrest. EMBO J; 29: 2407-20).

Methods

Cell lines obtained from the American Type Culture Collection (Manassas, Va.) included CRL 1831, HCT-116, HCT-15, MCF10A, MCF-7, MDA-231, HEC-1-A, H-460, and WI38. A2780CP cells were from the European Collection of Cell Cultures (Salisbury, UK); other cell lines were kind gifts from Dr. Patricia Kruk (University of South Florida, Tampa, Fla.) or from Dr. Andrew Berchuck or Dr. Susan Murphy (Duke University, Durham, N.C.) (OVCAR4, SNB-75, SF-539, UACC-62, SK-MEL-2, EKVX, 780-0, TK-10, IGROV1, and Nose7). Cell lines were supplemented with 10% fetal bovine serum, 1% sodium pyruvate, and 1% nonessential amino acids. All tissue culture reagents were obtained from Fisher Scientific (Pittsburgh, Pa.). *Mycoplasma* testing was performed every six months following manufacturer's protocol (Lonza, Rockland Me.).

BAD Pathway Expression

PCA was used to derive a BAD Pathway Gene Expression Signature score (BPGES) as previously described. (Marchion, et al., BAD phosphorylation determines ovarian cancer chemo-sensitivity and patient survival. Clin Cancer Res 2011 Oct. 1; 17(19):6356-66; Chen, et al., Proliferative genes dominate malignancy-risk gene signature in histologically-normal breast tissue. Breast Cancer Res Treat; 119: 335-46). The BPGES represents an overall similarity measure between samples based on their expression profile for the selected genes in the BAD pathway. In brief, PCA was applied to each dataset to reduce the data dimension into a small set of uncorrelated principal components, which were generated based on their ability to account for the systematic variation in the data. In the PCA model, the X matrix (gene expression values) can be described as follows: $X = t1^*p1' + t2^*p2' + t3^*p3' + \ldots + tA^*pA' + E$ (where ti represents scores, pi represents loading, and E represents residual matrix). The scores, ti, show how similar samples are to each other, and the loading, pi, explains which variables (genes) are important for principal component i. The first principal component (PC1), which accounts for the largest variability in the data, was used as the BPGES to represent the overall expression profile for the BAD pathway. It is known that directional signs of PCA scores are recognized to be arbitrary and can vary between software and algorithm used to calculate the PCA model (Jolliffe, Principal Component Analysis. 2 ed. New York: Springer; 2002). However, this does not affect the interpretation of the PCA model and can be easily solved by multiplying both scores and loadings by −1, a 180° rotation. Reflecting this, and for the sake of consistency, analyses of the PCA model were rotated so a high score corresponded to a normal sample or to an increased survival time.

BAD Pathway Expression and Cancer Development

BPGES was evaluated in a series of 6 genome-wide expression array datasets: 1) 185 breast samples (42 normal, 143 cancer) (GSE10780); 2) 22 colon samples (10 normal, 12 cancer) (GSE4107); 3) 107 lung samples (49 normal, 58 cancer) (GSE10072); 4) 61 breast samples (8 atypical ductal hyperplasia, 30 ductal carcinoma in situ, 23 invasive ductal carcinoma) (Ma, et al., Gene expression profiles of human breast cancer progression. Proc Natl Acad Sci USA 2003; 100: 5974-9); 5) 33 endometrium samples (9 normal, 4 hyperplastic, 20 cancer) (MCC data); and 6) normal endometrium and ovarian endometriosis samples, a postulated risk-factor/precursor to some ovarian cancers (n=20; 10 normal, 10 ovarian endometriosis samples) (GSE7305); and glioma (Nutt, et al., Gene expression-based classification of malignant gliomas correlates better with survival than histological classification. Cancer Res. 2003 Apr. 1; 63(7): 1602-7).

BPGES was evaluated between normal and pathologic tissues including normal versus hyperplasia, normal versus cancer, and carcinoma in situ versus cancer, etc. as determined by dataset availability.

BAD Pathway Expression and Patient Survival

The influence of BPGES was evaluated in 5 external clinico-genomic expression datasets, including: 1) 177 colon cancers, (Smith, et al., Experimentally derived metastasis gene expression profile predicts recurrence and death in patients with colon cancer. Gastroenterology; 138: 958-68); 2) 286 breast cancers, (Wang, et al., Gene-expression profiles to predict distant metastasis of lymph-node-negative primary breast cancer. Lancet 2005; 365: 671-9); 3) 155 tamoxifen-treated breast cancers, (Chanrion M, et al., A gene expression signature that can predict the recurrence of tamoxifen-treated primary breast cancer. Clin Cancer Res 2008; 14: 1744-52); 4) 50 malignant gliomas, (Nutt, et al., Gene expression-based classification of malignant gliomas correlates better with survival than histological classification. Cancer Res 2003; 63: 1602-7); and 5) 130 lung cancers (GSE4573).

The association between BPGES (high versus low score based on median BPGES score cutoff) and clinical outcome was evaluated. Kaplan-Meier survival curves were generated, and high/low BAD-pathway score survival differences were evaluated using log-rank tests in 1) colon cancer patients, (Marchion, et al., BAD phosphorylation determines ovarian cancer chemo-sensitivity and patient survival. Clin Cancer Res. 2011 Oct. 1; 17(19):6356-66); 2) breast cancer patients, (Wang, et al., Gene-expression profiles to predict distant metastasis of lymph-node-negative primary breast cancer. Lancet 2005; 365: 671-9); 3) tamoxifen-treated breast cancer patients, (Chanrion, et al., A gene expression signature that can predict the recurrence of tamoxifen-treated primary breast cancer. Clin Cancer Res 2008; 14: 1744-52); 4) brain cancer patients, (Nutt, et al., Gene expression-based classification of malignant gliomas correlates better with survival than histological classification. Cancer Res 2003; 63: 1602-7); and 5) lung cancer patients (GSE4573). Log-rank test P values indicate significance.

Analysis of Genomic and Chemo-Sensitivity Data for NCI60 Cancer Cell Lines

Affymetrix HG-U133A expression and GI50 chemosensitivity data for the 60 NCI cancer cell lines (6 leukemia, 9 melanoma, 9 non-small cell lung (NSCLC), 7 colon, 6 central nervous system, 7 ovarian, 8 renal, 2 prostate, and 6 breast cancer cell lines) to cisplatin, carboplatin, doxorubicin, gemcitabine, paclitaxel, docetaxel, and topotecan were obtained from the NCI. For each of the eight drugs, gene expression data from the most sensitive and resistant cell lines (cutoff=mean GI50-standard deviation) were compared using significance analysis of microarray t-test (SAM t-test, false discover rate of <20%) (Efron and Tibshirani, Empirical bayes methods and false discovery rates for microarrays. Genet Epidemiol 2002; 23: 70-86; Tusher V G, et al., Significance analysis of microarrays applied to the ionizing radiation response. Proc Natl Acad Sci USA 2001; 98: 5116-21) and subjected to GeneGo/MetaCore™ pathway analyses. Information was available for 59/60 cell lines.

Modulating BAD Phosphorylation by siRNA Transfection

Because many genes in the BAD pathway influence the phosphorylation status of the BAD protein, either directly or indirectly, the phenotypic consequences of modulation of BAD phosphorylation levels were explored. RNA duplexes for CDK1 (cdc2, ID# s464) and PP2C (PPM1A, ID# s10919) were purchased from Applied Biosystems (Foster City, Calif.). Cells were transfected by electroporation using the Nucleofector transfection kit according to the manufacturer's recommendations (Lonza, Basel, Switzerland). Cells (4×106) were suspended in 0.1 mL of electroporation buffer V containing 1 µM siRNA. The X-001 program was used to electroporate OVCAR 4, HEC-1-A, and HCT-15 cell lines, whereas MCF-7 and MDA-231 cells were electroporated using the E-014 and X-005 programs, respectively. All siRNAs were used at a final concentration of 1 µM. Electroporated cells were incubated at 37° C. for 15 minutes before plating. The Silencer Select Negative Control #2 siRNA (catalog no. 4390846, Applied Biosystems), a non-sense siRNA duplex, was used as a control. Cell pellets were collected 96 hours later to check for transfection efficiency.

MTS Cell Proliferation Assays

Following transfection, each cell line was seeded in 96-well plates at a density of 2,500 cells/well, in triplicate and for two different time points. Incubation ended 24 and 72 hours after transfection. At both time points, MTS solution was added at a final concentration of 0.5 mg/mL. Plates were incubated for 2 hours at 37° C., and absorbance at 490 nm was detected at 0.1-s intervals using a 1420 multi-label VICTOR2 ™ counter (Wallac, Perkin-Elmer Life Sciences). Cell growth at 72 hours was expressed as percent of 24-hour cell attachment/growth.

Western Blot Analysis

Cells were harvested in media using a cell lifter and washed with cold phosphate-buffered saline (PBS) containing 1× phosphatase inhibitor cocktail (Sigma-Aldrich, St. Louis, Mo.). Lysates were prepared with SDS lysis buffer (2% SDS, 10% glycerol, 0.06 M Tris, pH 6.8) and evaluated for protein concentration using the bicinchoninic acid (BCA) method (Pierce, Rockford, Ill.). Proteins (75 µg) were separated on the same day as collection time on 12-15% SDS-PAGE gels and transferred to polyvinylidene fluoride membranes. Membranes were blocked with 5% nonfat milk in Tris-buffered saline containing 0.05% Tween 20 (TBST) and incubated with primary antibody in 5% nonfat milk in TBST overnight at 4° C. Membranes were washed three times for 5 minutes with TBST and incubated with the appropriate secondary antibody in 5% nonfat milk in TBST for 60 minutes at room temperature. Membranes were washed four times for 5 minutes with TBST prior to antibody binding visualization by Super Signal West Pico chemiluminescence solution (Pierce) on autoradiography film (Midwest Scientific, St. Louis, Mo.).

Immunofluorescence Microscopy

Cells were seeded in 12-well plates at a density of 20,000/well for 24 hours before fixation with 95% ethanol-5% acetic acid solution for 1 minute. After three washes with PBS, cells were incubated overnight in 2% bovine serum albumin (BSA) solution in PBS. Cells were exposed to primary antibody in blocking serum, 2% BSA (Sigma-Aldrich) in PBS for 24 hours at 4° C., and then washed five times for 5 minutes each with 1% BSA solution, followed by incubation with fluorescent-labeled secondary antibody in blocking serum for 1 hour at room temperature. All wells were counterstained and mounted with Prolong Gold containing DAPI (Invitrogen). Images were acquired as TIFF files using a fully automated, upright Zeiss Axio-ObserverZ.1 microscope, x20/0.4 NA objective, and DAPI, FITC, and rhodamine filter cubes. Images were produced using the AxioCam MRm CCD camera and Axiovision version 4.7 software suite (Carl Zeiss Inc). Exposure times were identical for each antibody across the cell lines pairs. Intensity of fluorescence for each image was determined using Definiens Developer XD 1.5 software. An algorithm was developed to extract the fluorescence intensity per cell. Immunofluorescence intensity of each cancer cell line is expressed relative to the intensity of same tissue type immortalized cell line.

Antibodies

Antibodies were as follows: phosphorylated BAD (pBAD)-112, -136, and -155 (Genscript, Piscataway, N.J.); BAD (Cell Signaling Technology, Danvers, Mass.); PP2C Western (Santa Cruz Biotechnology, Santa Cruz, Calif.), PP2C immunofluorescence (Abgent, San Diego, Calif.); CDK (Santa Cruz Biotechnology); pAKT, AKT, pPKA, and PKA (Cell Signaling Technology, Danvers, Mass.); GAPDH (Millipore, Billerica, Mass.); anti-mouse IgG and anti-rabbit IgG (Amersham Biosciences, Buckinghamshire, UK); and AlexaFluor® 488 goat anti-mouse IgG, AlexaFluor® 546, and goat anti-rabbit IgG (Invitrogen, Eugene, Oreg.).

Results

BAD Pathway Expression is Associated with Cancer Development, Progression, Relapse, and Survival Statistically significant differences in mean BPGES were identified between normal tissue and corresponding invasive carcinomas in two of three datasets (n=314) (FIG. 1). Normal breast samples (n=143) had a mean BPGES of 0.935 versus −2.84 for invasive breast cancer samples (n=42, P<0.001) (FIG. 1A). Normal colon samples (n=12) had a mean BPGES of 4.049 versus −3.374 in invasive colon cancer samples (n=12, P<0.001) (FIG. 1B). Normal lung samples (n=49) had a mean BPGES of 0.623 versus −0.527 in the lung cancer samples (n=58, P=0.177), although this difference did not reach statistical significance (FIG. 1C).

BPGES was also evaluated in 3 datasets (n=114) for which data were available that reflected the transition of tissues from normal to pre-invasive to invasive cancer. Overall, as shown by BPGES, there were consistent differences between normal tissue and pre-invasive tissue, with cancer BPGES scores consistently lower than normal, and between pre-invasive and invasive disease. The transition of breast tissue atypical ductal hyperplasia (ADH) to ductal carcinoma in situ (DCIS), to invasive ductal carcinoma (IDC), correlated with progressive changes in BPGES (Spearman correlation estimate=−0.264, P=0.04, FIG. 1D).

Figure 1E:
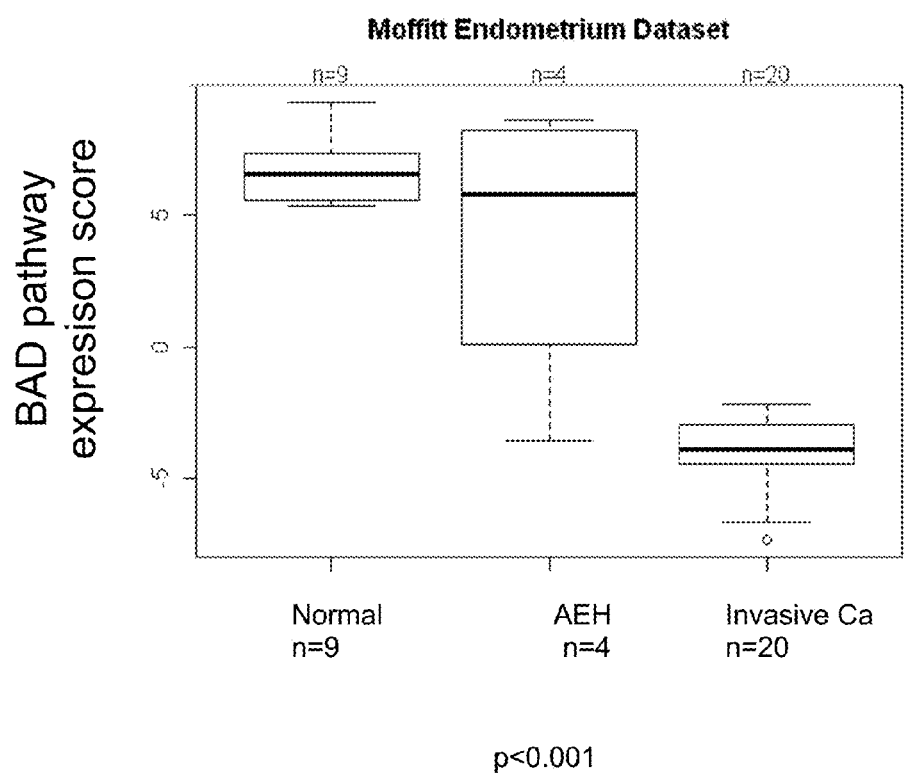

As shown in FIG. 1E, BPGES was consistently correlated with the transition of normal endometrial tissue (mean=6.745, n=9) to atypical endometrial hyperplasia (AEH; mean=4.161), to invasive endometrial cancer (mean=−3.867, n=20) (Spearman correlation estimate=−0.795, P<0.001).

Figure 1F:
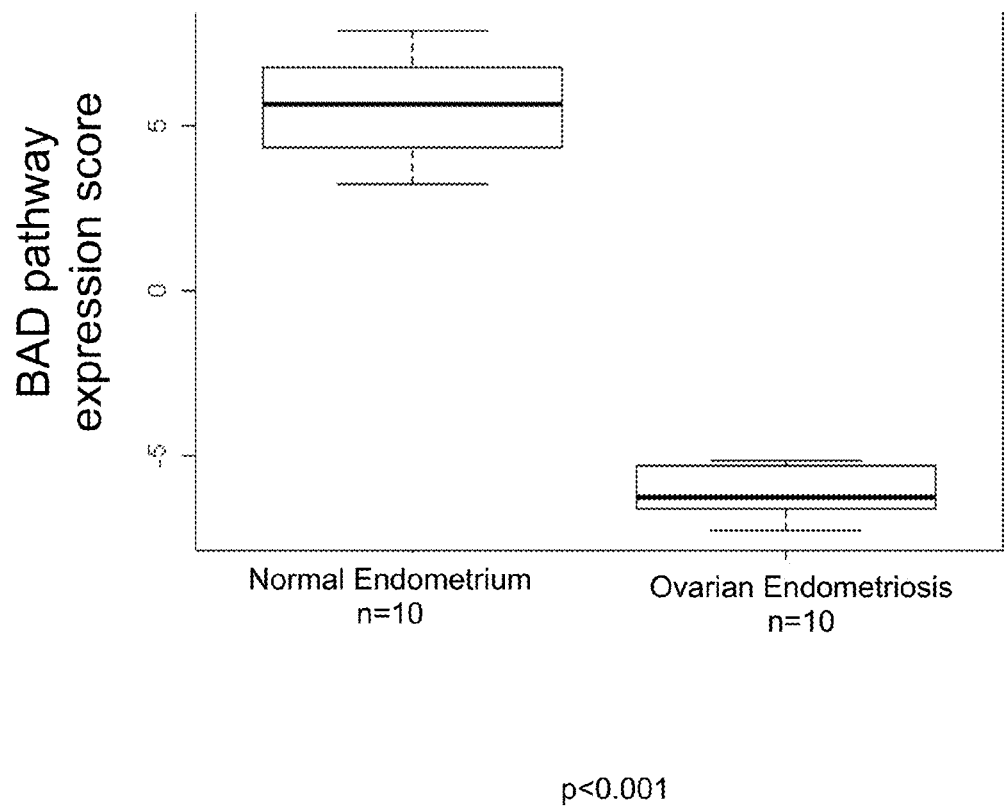

Ovarian endometriosis is a recognized risk factor for some types of ovarian cancer. The expression of the BAD pathway was therefore evaluated in normal endometrial tissue and ovarian endometriosis. As shown in FIG. 1F, mean BPGES demonstrated significant differences (P<0.001) between normal endometrium (mean=5.614, n=10) and ovarian endometrioses samples (mean=−5.614, n=10).

Figure 2A:
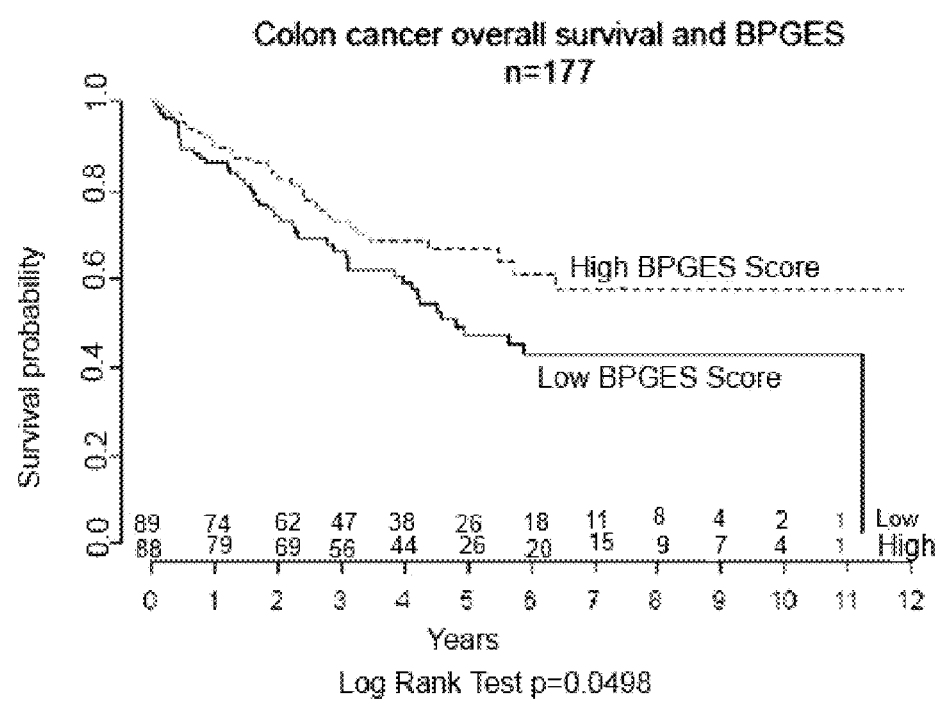
FIG. 2A-E is a series of images depicting that the BPGES correlates with survival probability. The potential relation between the BAD pathway activity and clinical outcome was explored in 5 external clinico-genomic datasets representing multiple tumor types from 826 patient samples total. Kaplan-Meier curves depict the association between survival and BPGES in (A) colon cancer (n=205, P=0.005); (B) relapse-free breast cancer (n=286, P=0.01); (C) relapse-free breast cancer, tamoxifen-treated (n=155, P=0.02); (D) brain cancer (n=50, P=0.01); and (E) lung cancer (n=130, P=0.814). The numbers at risk are shown at the bottom of the graphs. Log-rank test P values indicate significance.
Figure 2B:
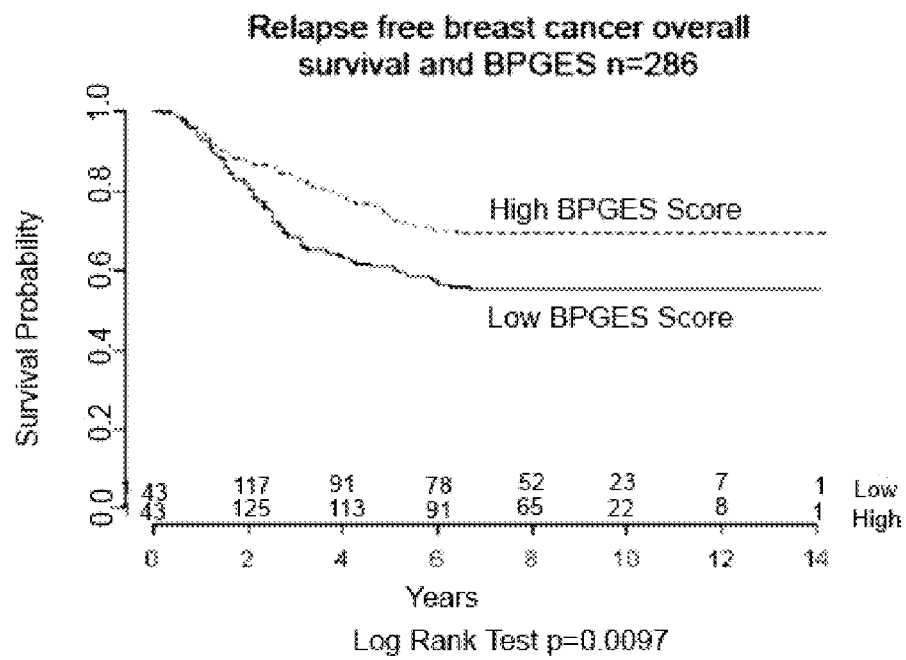
Figure 2C:
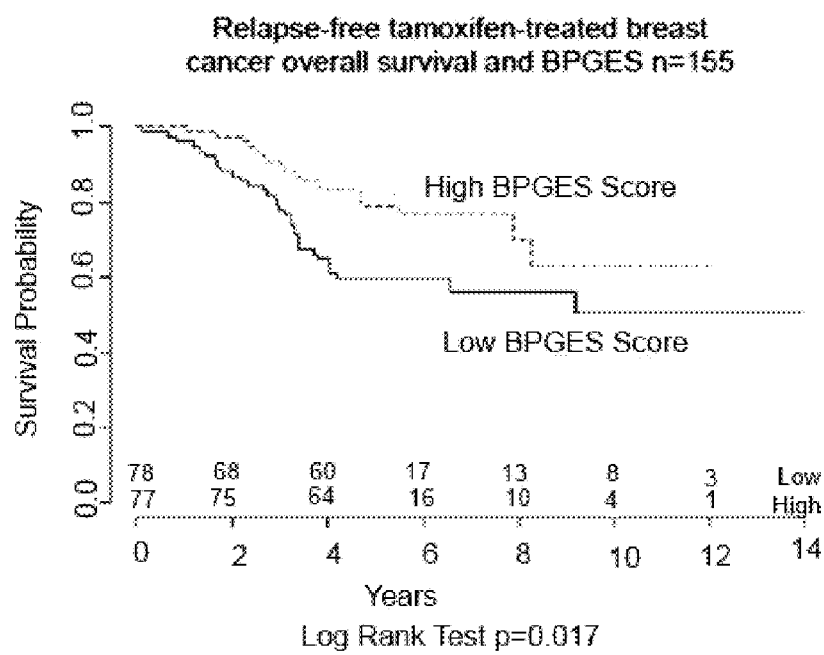
Figure 2D:
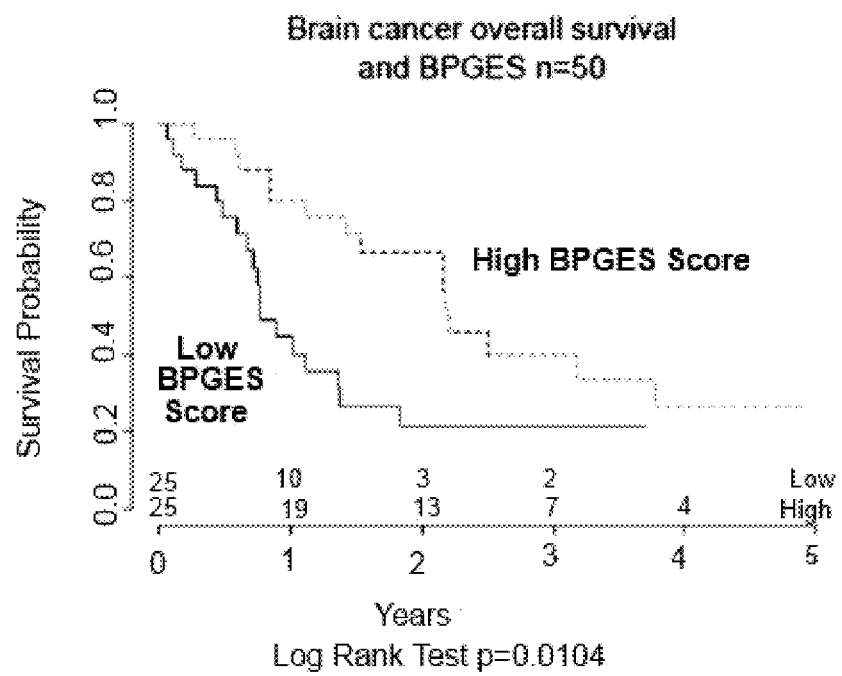
Figure 2E:
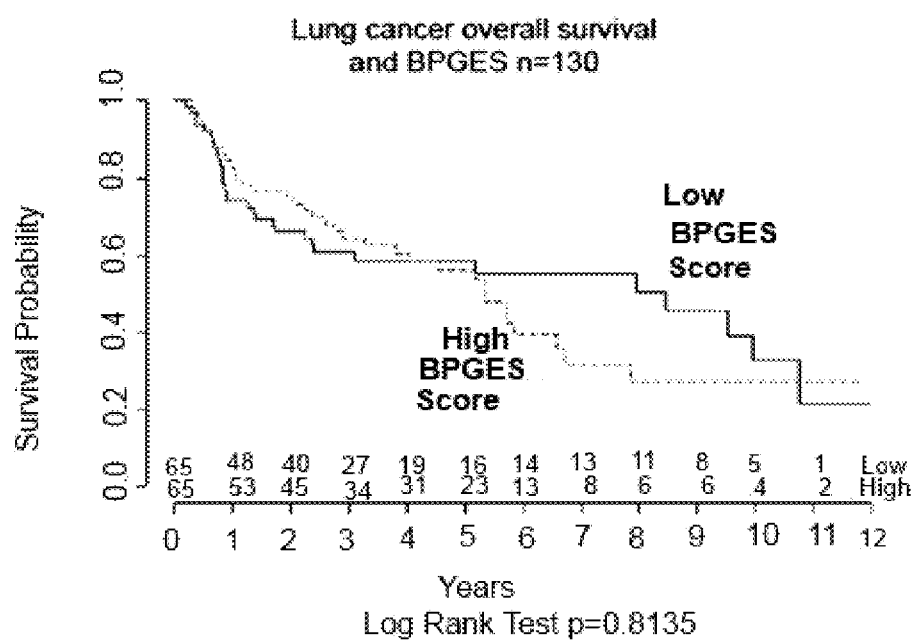

BAD pathway expression was evaluated for associations with patient survival in 5 external clinico-genomic datasets representing multiple tumor types from 798 patient samples. Using median BPGES score as a cut-off to dichotomize samples for analysis, an association between BPGES and overall survival was identified for colon cancer (n=177, P=0.05; FIG. 2A), relapse-free survival from breast cancer (n=286, P=0.01; FIG. 2B) and tamoxifen-treated breast cancer (n=155, P=0.02, FIG. 2C), and brain cancer (n=50, P=0.01; FIG. 2D), but not lung cancer (n=130, P=0.814; FIG. 2E). See also, FIG. 8.

BAD Pathway Expression is Associated with In-Vitro Sensitivity to a Broad Range of Cytotoxic Drugs To explore associations between BAD pathway expression and responsiveness of multiple cancer cell types to a variety of cytotoxic drugs commonly used in clinical practice to treat patients with cancer, genomic and chemosensitivity data for the NCI60 cancer cell line panel was evaluated. When all cell types were analyzed together, GeneGo/MetaCore™ identified representation of the BAD pathway in genes differentially expressed in cells sensitive versus those resistant to carboplatin (P<0.001), paclitaxel (P=0.015), and gemcitabine (P=0.001), but not to docetaxel, doxorubicin, topotecan, or cisplatin (FIG. 6). Similarly, this NCI dataset was analyzed by each distinct cancer cell type for representation of the BAD pathway associated with sensitivity to individual drugs. Thus, the BAD pathway was associated with chemosensitivity of OVCA cells to carboplatin (P=0.01), breast cancer cells to carboplatin (P=0.04) and topotecan (P=0.03), leukemia cells to carboplatin and gemcitabine (P=0.03), melanoma cells to paclitaxel (P=0.02), and colon cancer cells to paclitaxel and docetaxel (P=0.03) (FIG. 7).

BAD Pathway Expression is Associated with In Vitro Levels of Phosphorylated BAD Protein To explore the biologic and functional bases to the associations observed between BPGES and various clinicopathologic features and because increased BAD phosphorylation at serine residues -112, -136, and -155 has been associated with changes to BAD protein interactions with BCL2 family apoptotic proteins, and hence resistance to apoptotic stimuli, the relationship between BAD phosphorylation status and BPGES was evaluated. BPGES and pBAD were measured in relatively chemo-sensitive and chemo-resistant cell pairs (using publicly available NCI60 GI50 data) including breast cancer (MCF-7, MDA-231), glioma (SNB-75, SF-539), melanoma (UACC-62, SK-MEL-2), and NSCLC (H-460, EKVX). For most cell pairs tested, differences in BPGES were observed between cells with high and low levels of pBAD at serine-155 (FIGS.

Figure 3A:
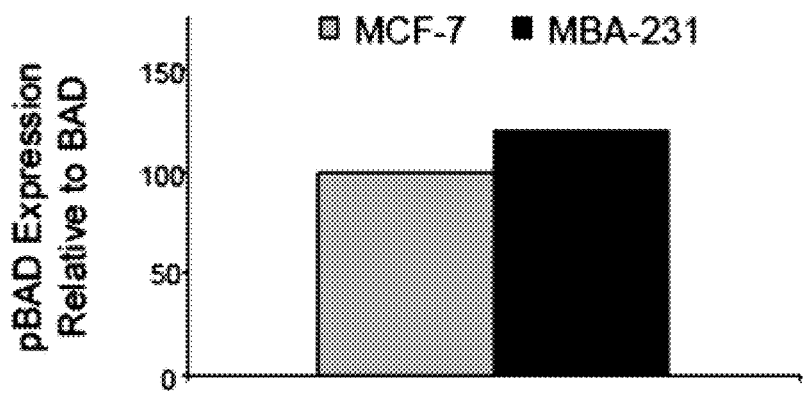
FIG. 3 is a series of images depicting that BPGES is inversely related to BAD phosphorylation levels. (A and B) Chemo-sensitive and -resistant breast cancer (MCF-7, MDA-231), (C and D) glioma (SNB-75, SF-539), (E and F) melanoma (UACC-62, SK-MEL-2), and (G and H) non-small cell lung carcinoma (H-460, EKVX) cell line pairs were evaluated for pBAD[ser-155] levels by immunofluorescence and BPGES score. For most cell lines tested, the BPGES score was capable of differentiating between cells with high versus low pBAD levels, with the exception of lung carcinoma cell lines (I-N). Chemoresistant cell lines express higher levels of pBAD protein by Western blot with the exception of the lung cancer cells (data not shown).
Figure 3B:
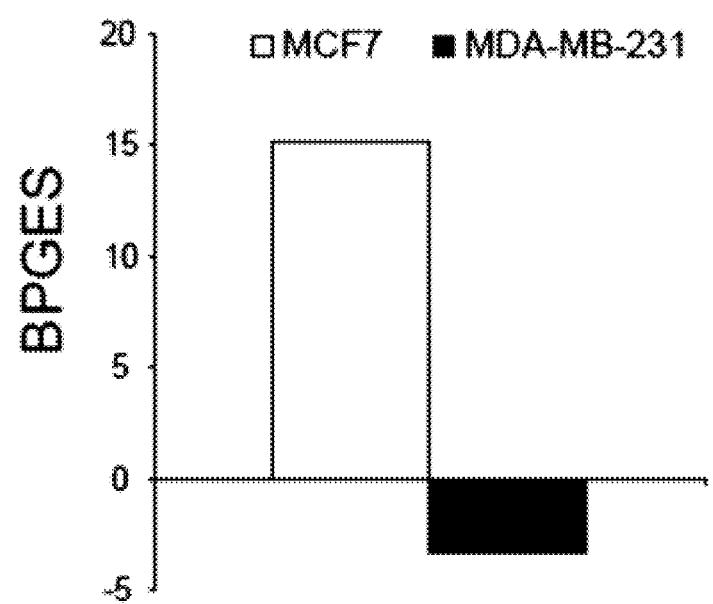
Figure 3C:
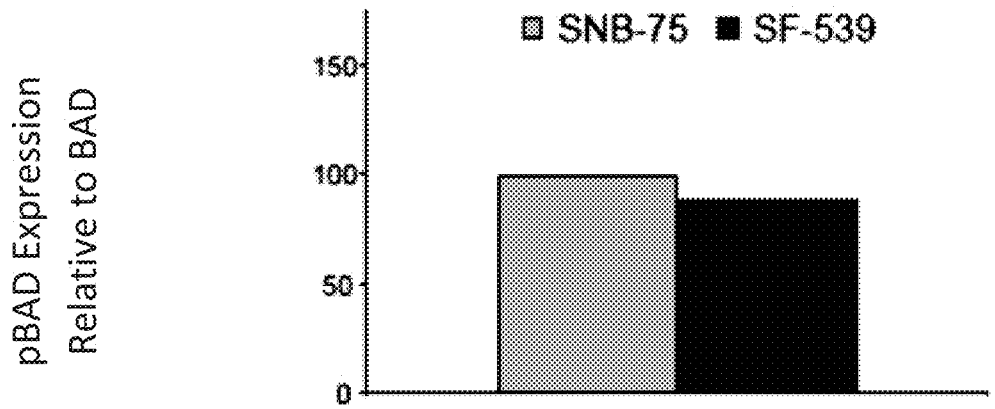
Figure 3D:
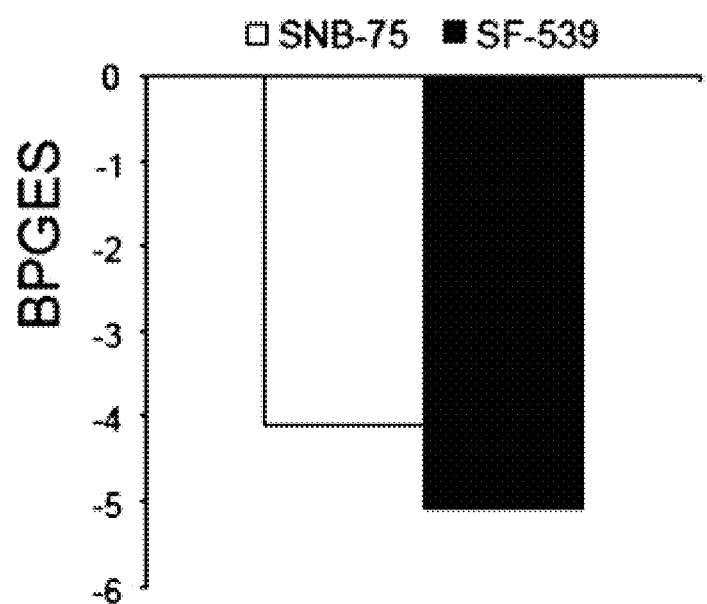
Figure 3E:
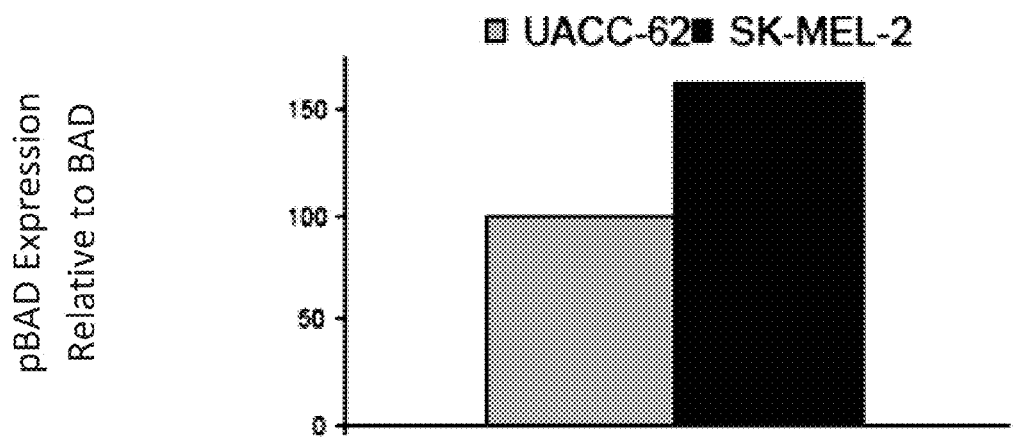
Figure 3F:
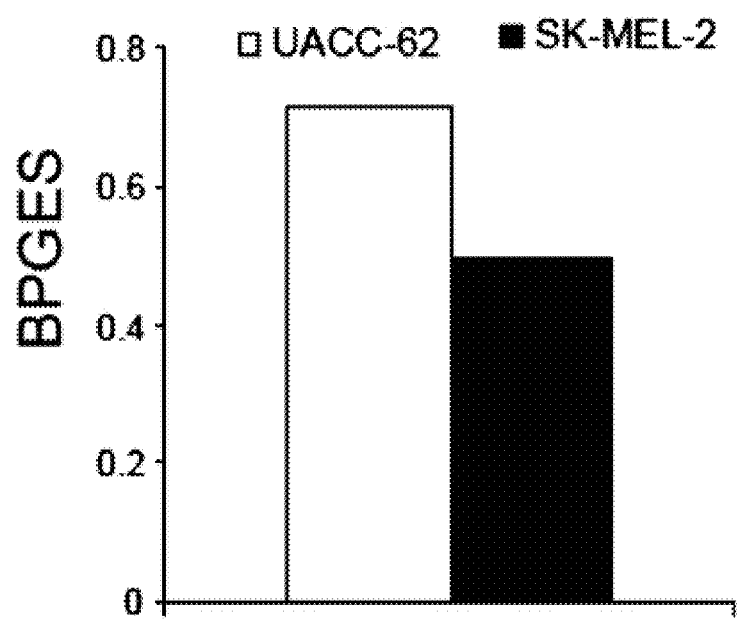
Figure 3G:
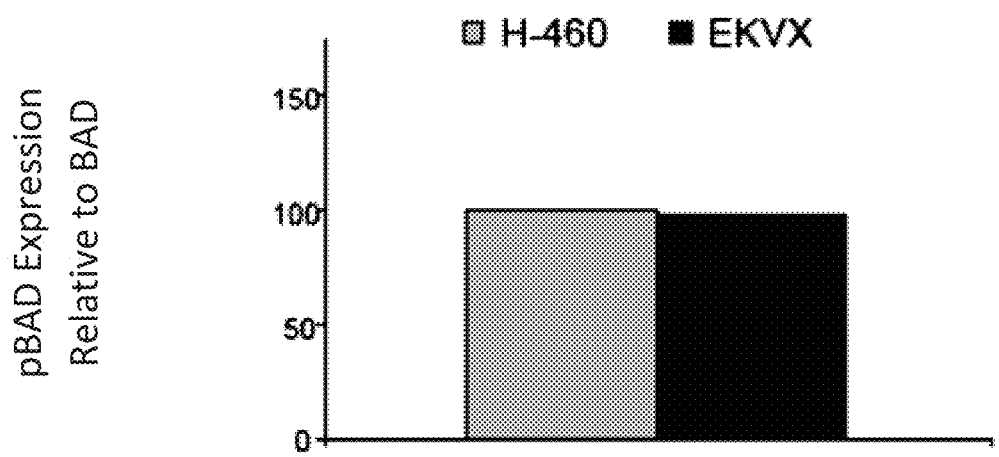
Figure 3H:
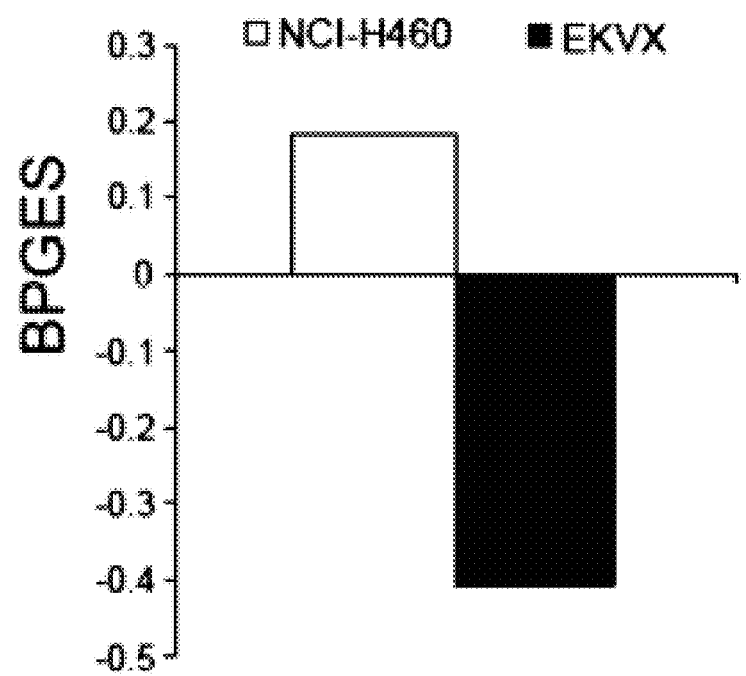
Figure 3I:
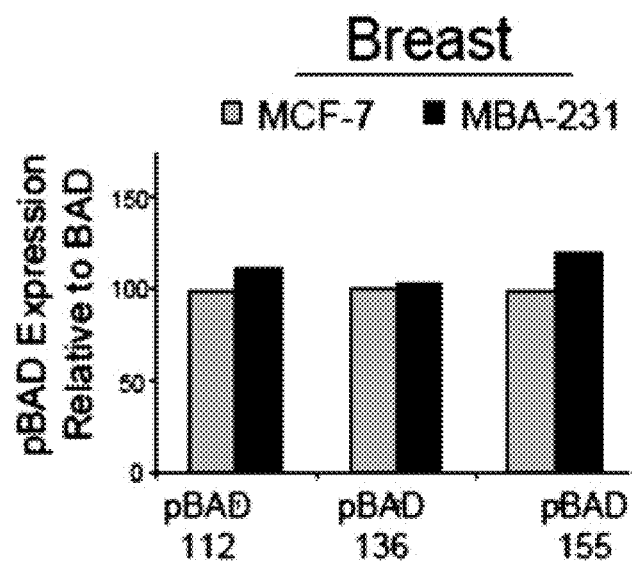
Figure 3J:
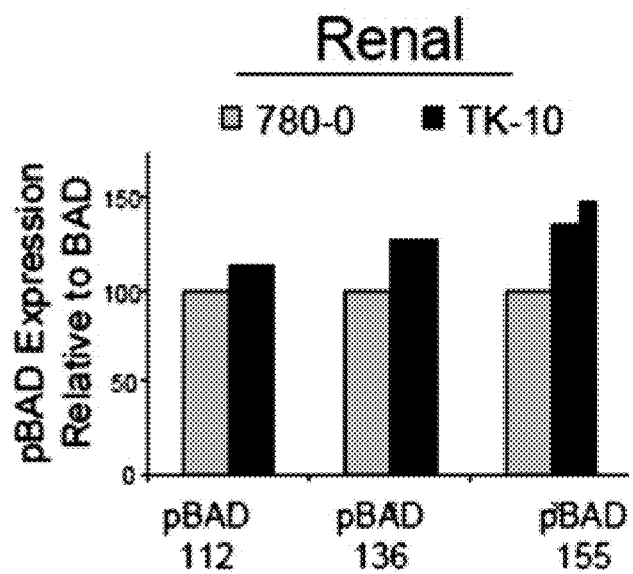
Figure 3K:
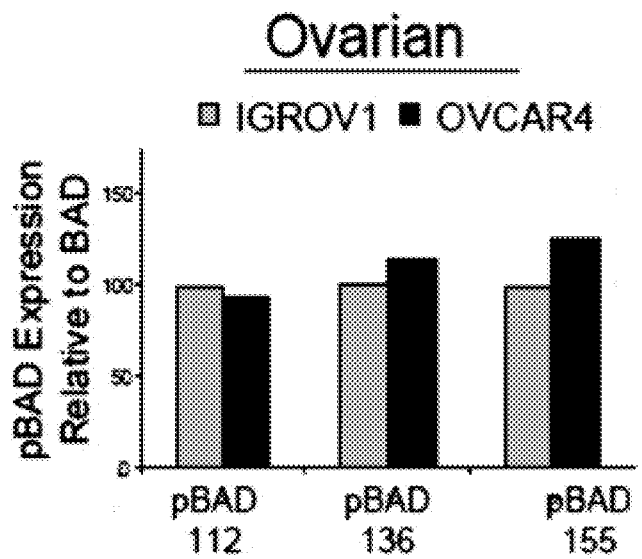
Figure 3L:
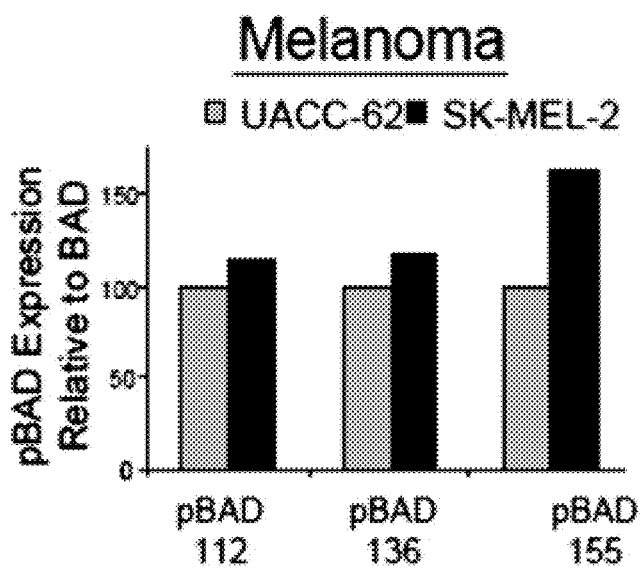
Figure 3M:
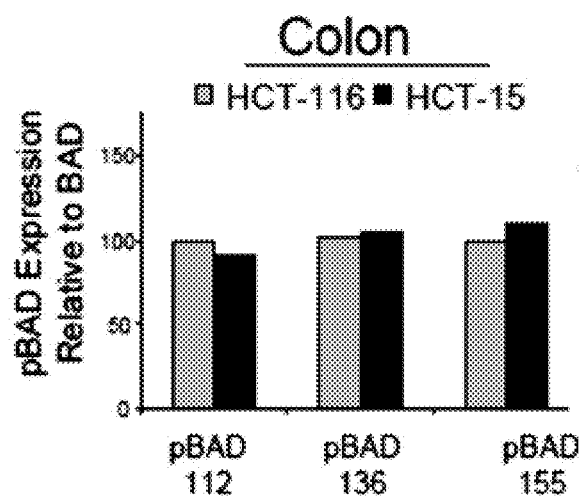
Figure 3N:
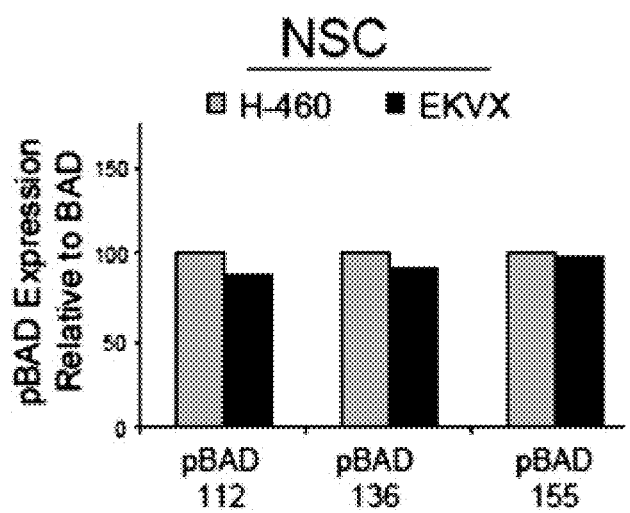
Figure 4A:
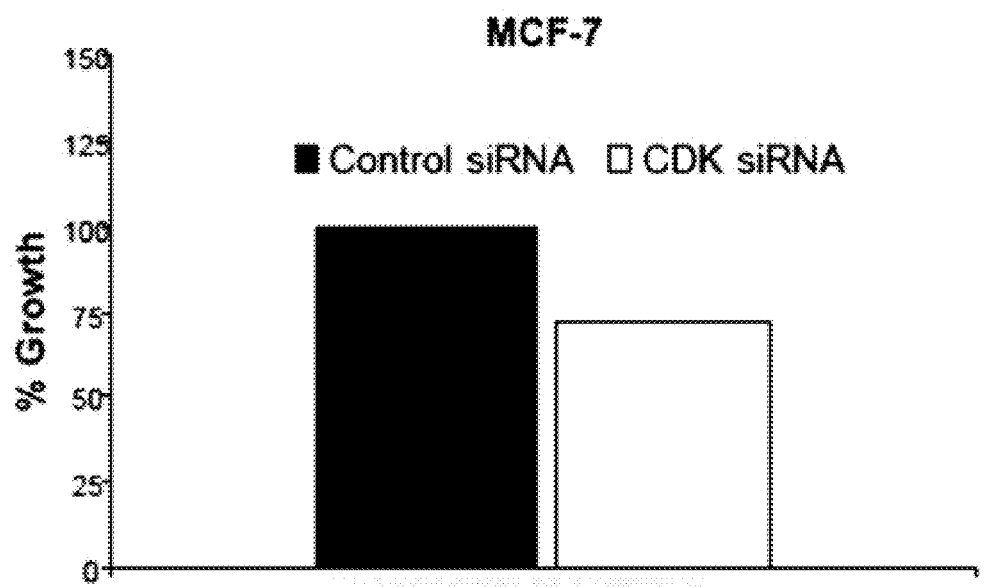
FIG. 4A-L is a series of images depicting modulation of BAD phosphorylation affects cancer cell proliferation. Depletion of the BAD protein kinase CDK1 resulted in decreased cell proliferation in (A and B) breast (MCF-7), (C and D) ovarian (OVCAR-4), and (E and F) colon (HCT-15) cancer cells, while depletion of the BAD protein phosphatase PP2C resulted in increased cell proliferation in MCF-7 and MBA-MD-231 breast cancer cells as well as in HEC-1-A endometrial cancer cells (G-L).
Figure 4B:
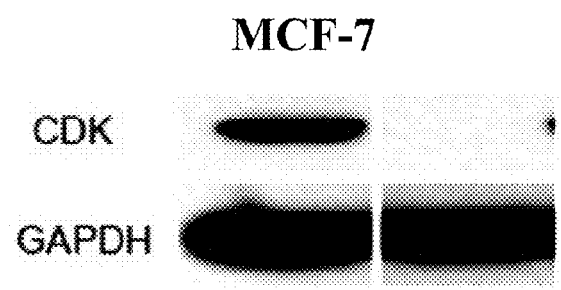
Figure 4C:
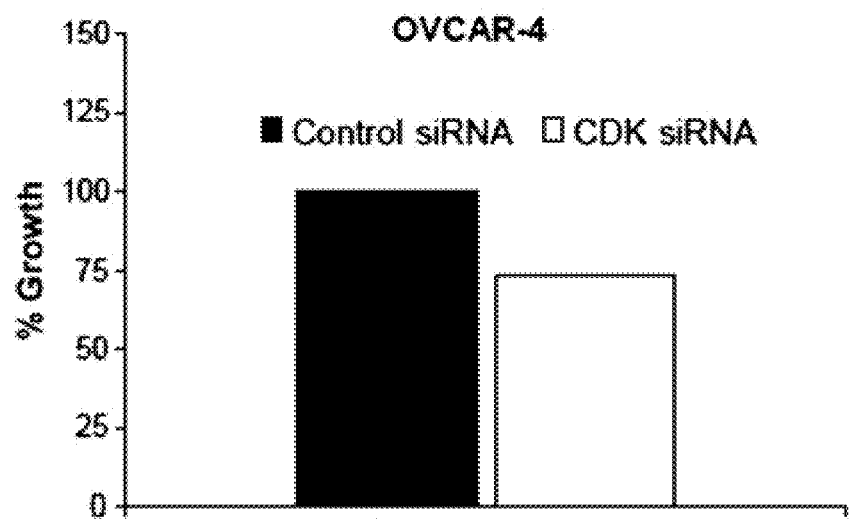
Figure 4D:
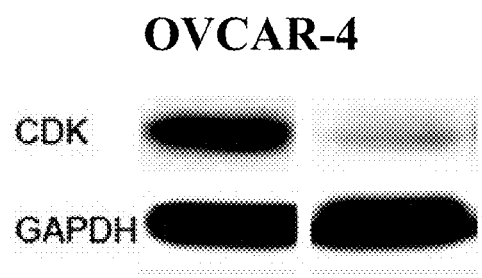
Figure 4E:
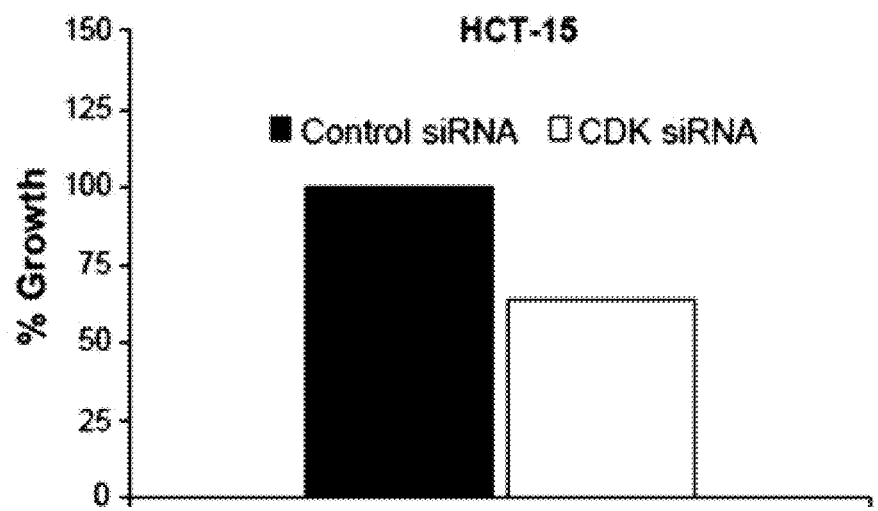
Figure 4F:
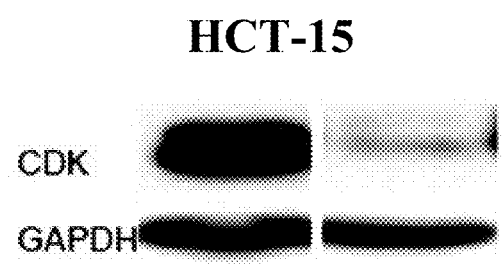
Figure 4G:
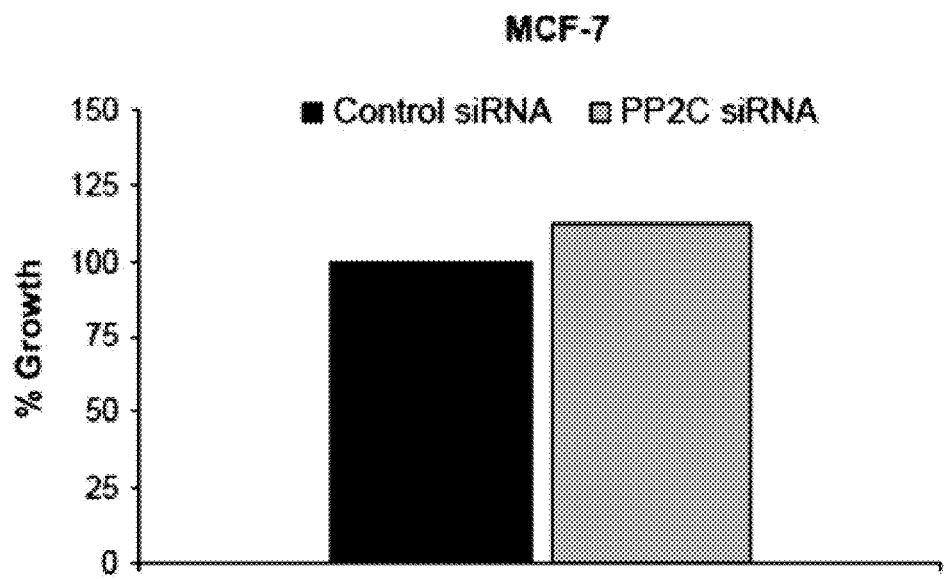
Figure 4H:
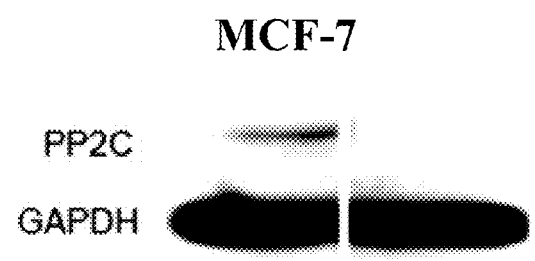
Figure 4I:
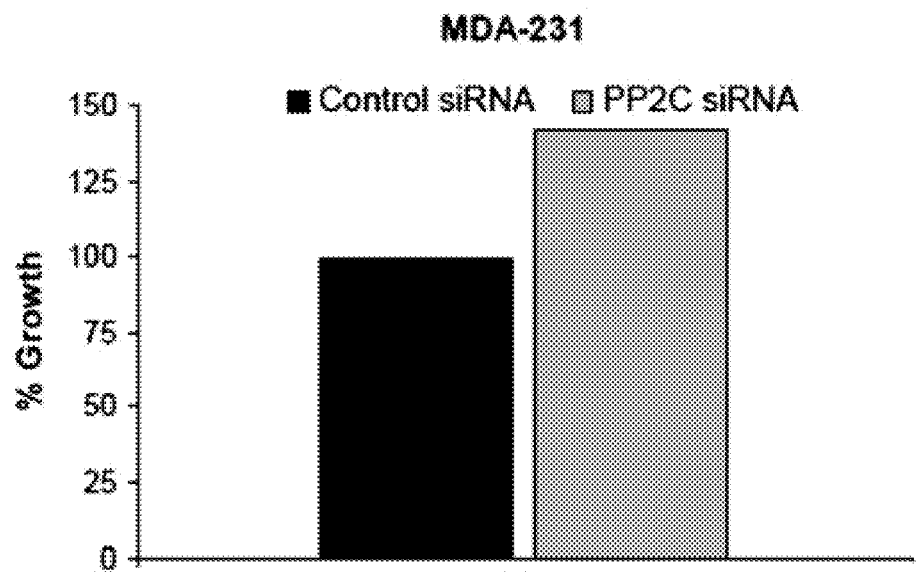
Figure 4J:
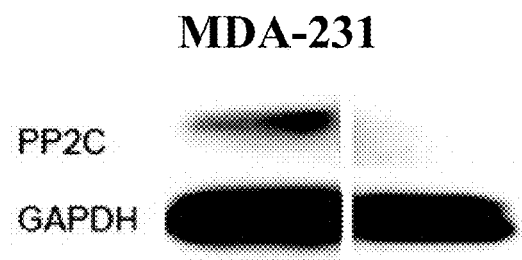
Figure 4K:
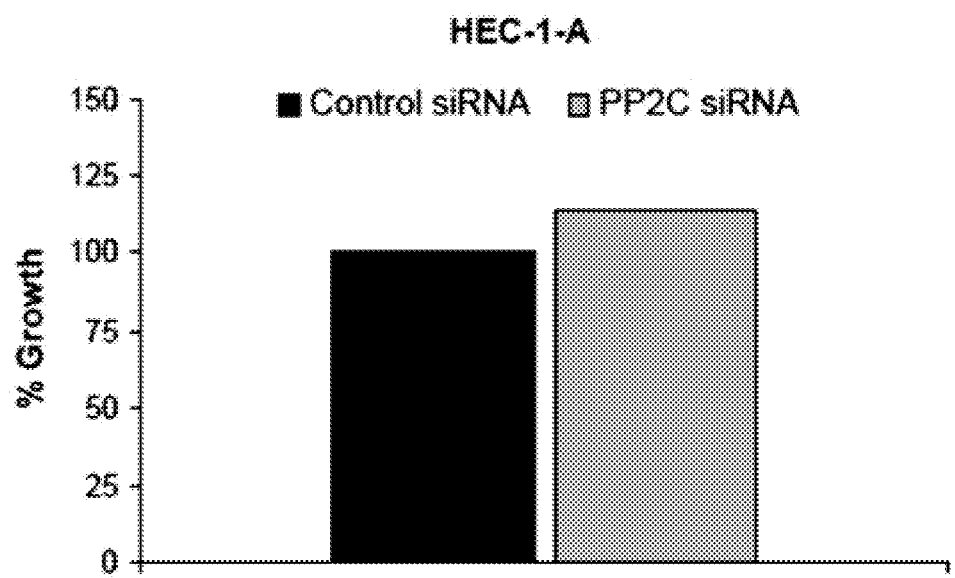
Figure 4L:
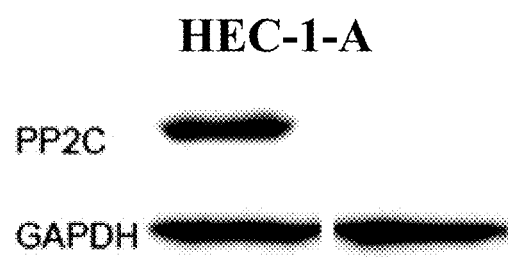
Figure 5A:
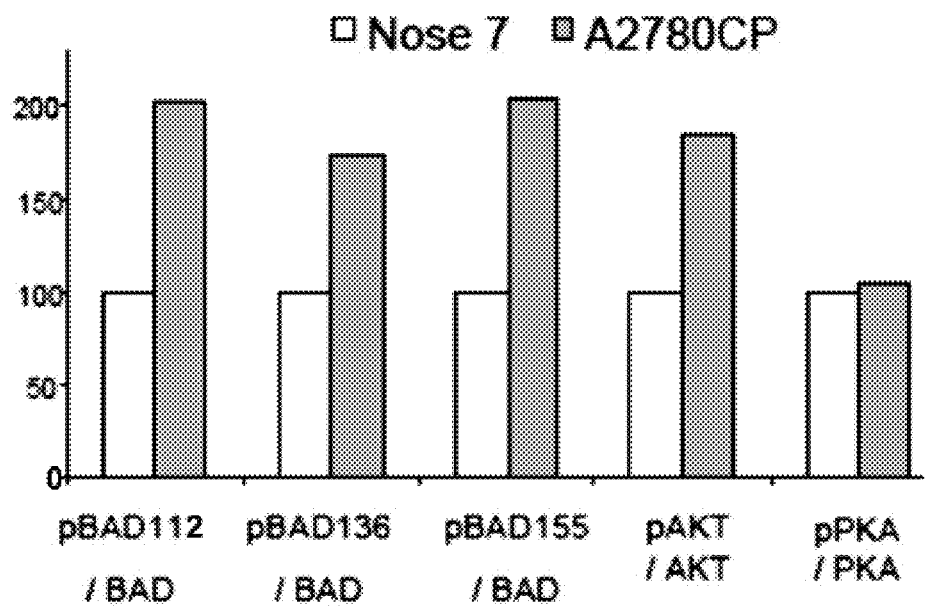
FIG. 5A-H is a series of images depicting BAD phosphorylation status and cancer development. Using immunofluorescence staining, expression levels of pBAD (serine-112, -136, -155), total BAD, pPKA, total PKA, pAKT, and AKT were compared between an immortalized cell line and a cancer cell line from a variety of tissue types, including (A and E) ovarian (Nose7 versus A2780CP), (B and F) colon (CRL1831 versus HCT-15), (C and G) breast (MCF10A versus MDA-231), and (D and H) lung (WI38 versus H-460). Relative to the normal samples, cancer cells expressed higher levels of pBAD (serine-112, -136 and -155) as well as one or more kinases known to phosphorylate BAD (PKA, AKT). The lung set was an exception to this observation.
Figure 5B:
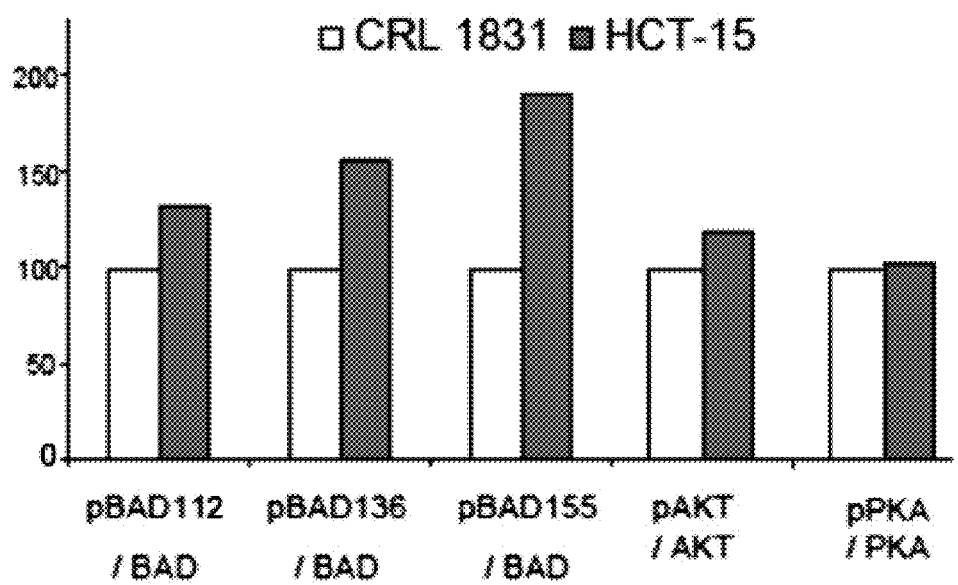
Figure 5C:
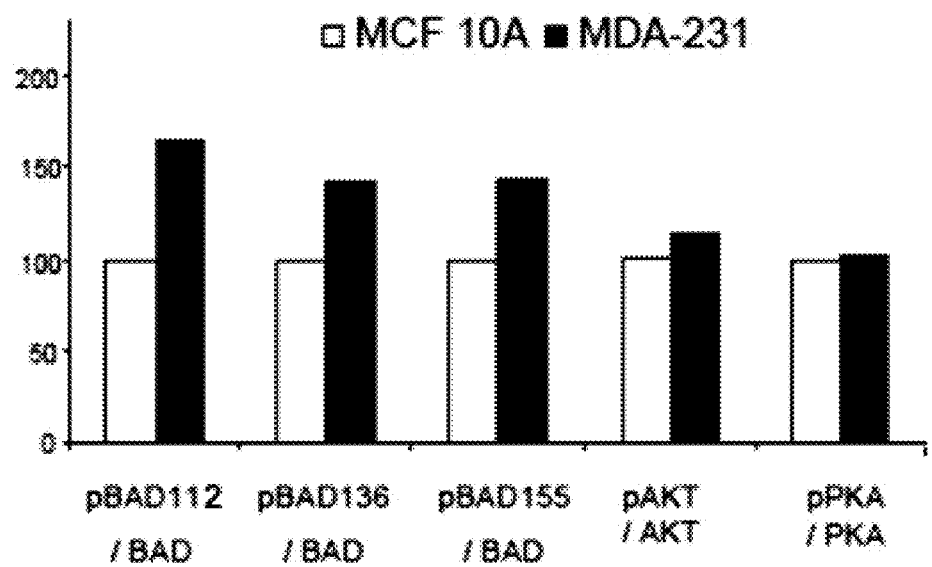
Figure 5D:
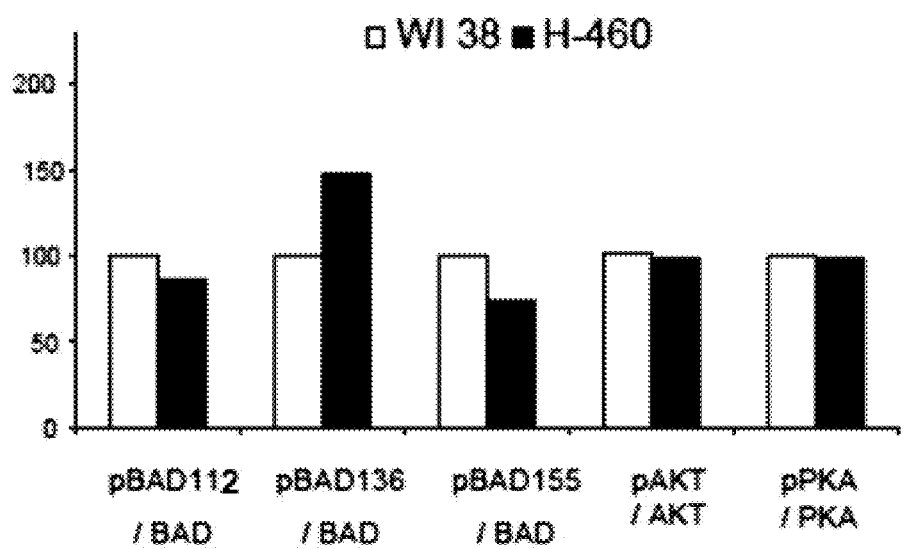
Figure 5E:
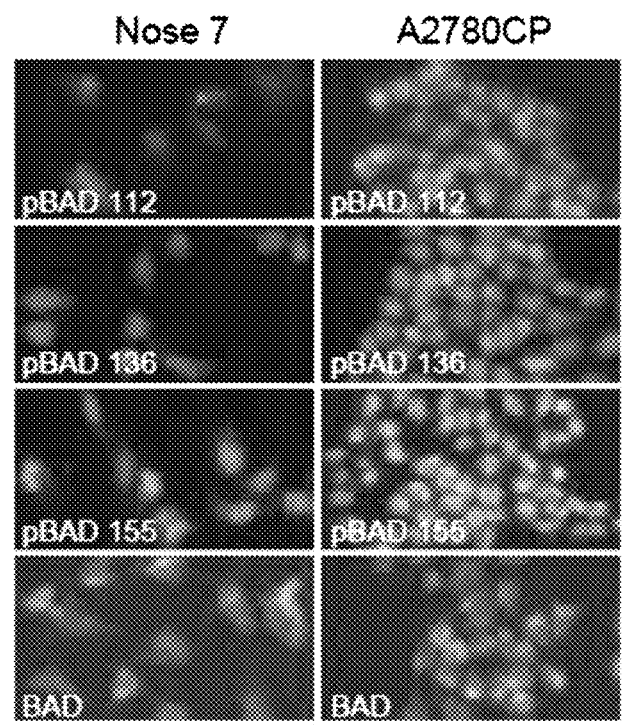
Figure 5F:
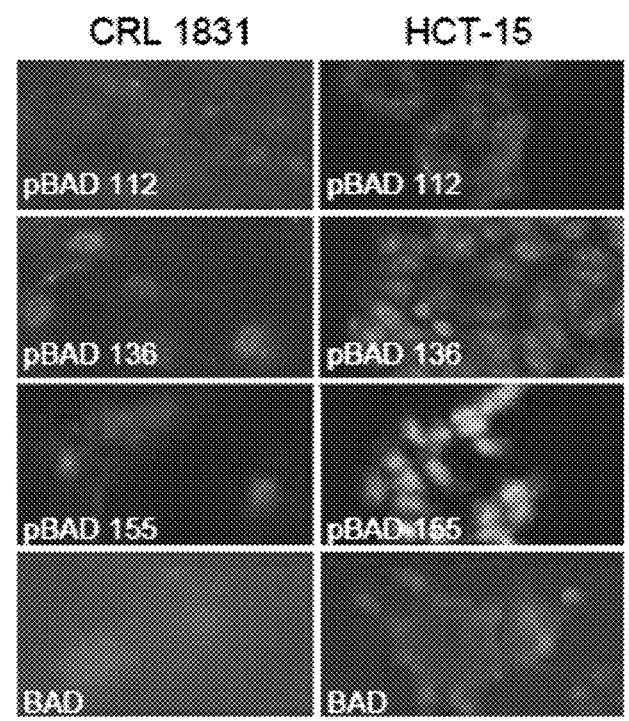
Figure 5G:
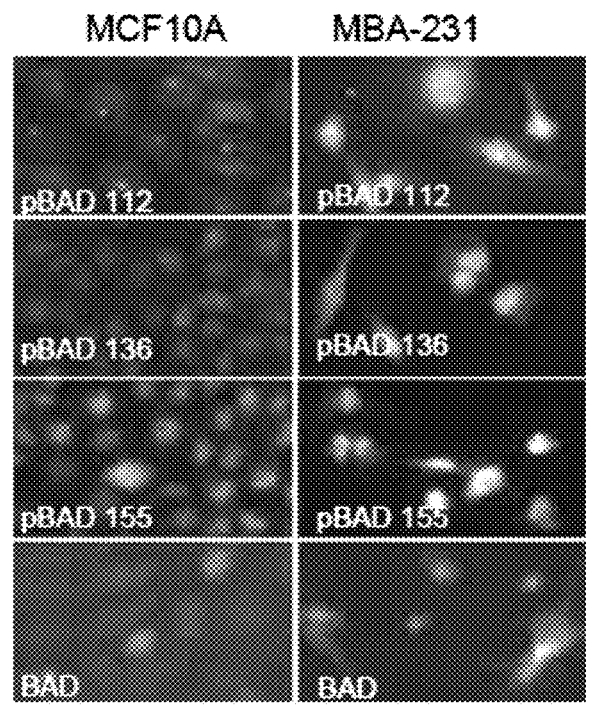
Figure 5H:
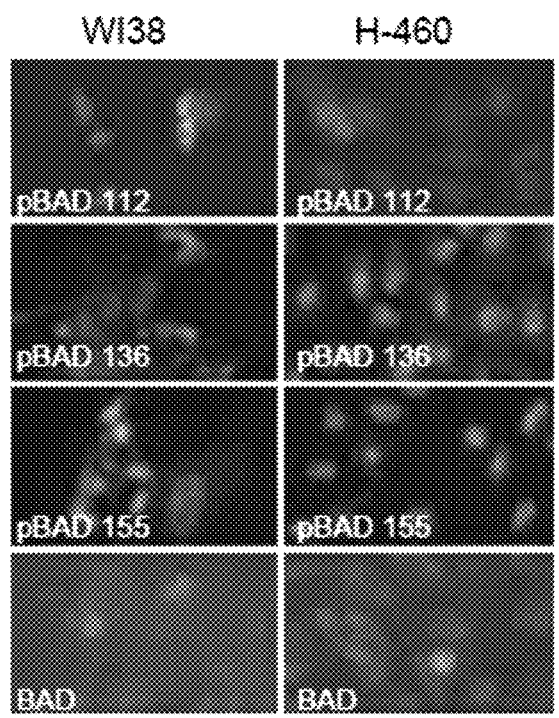
Figure 8A:
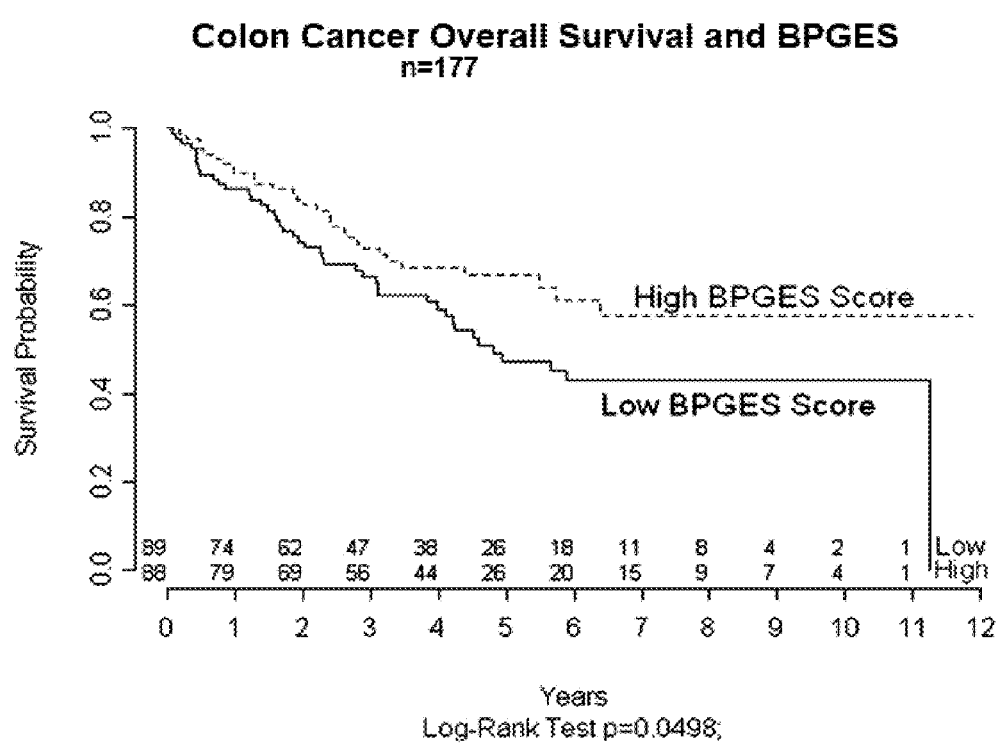
FIG. 8A-D is a series of images depicting the BAD pathway gene expression signature (BPGES) score is associated with overall patient survival. The BPGES score was tested in datasets representing multiple tumor types. Kaplan- Meier curves depict the association between survival and BPGES in (A) colon cancer, (B) brain cancer, (C) breast cancer, and (D) lung cancer.
Figure 8B:
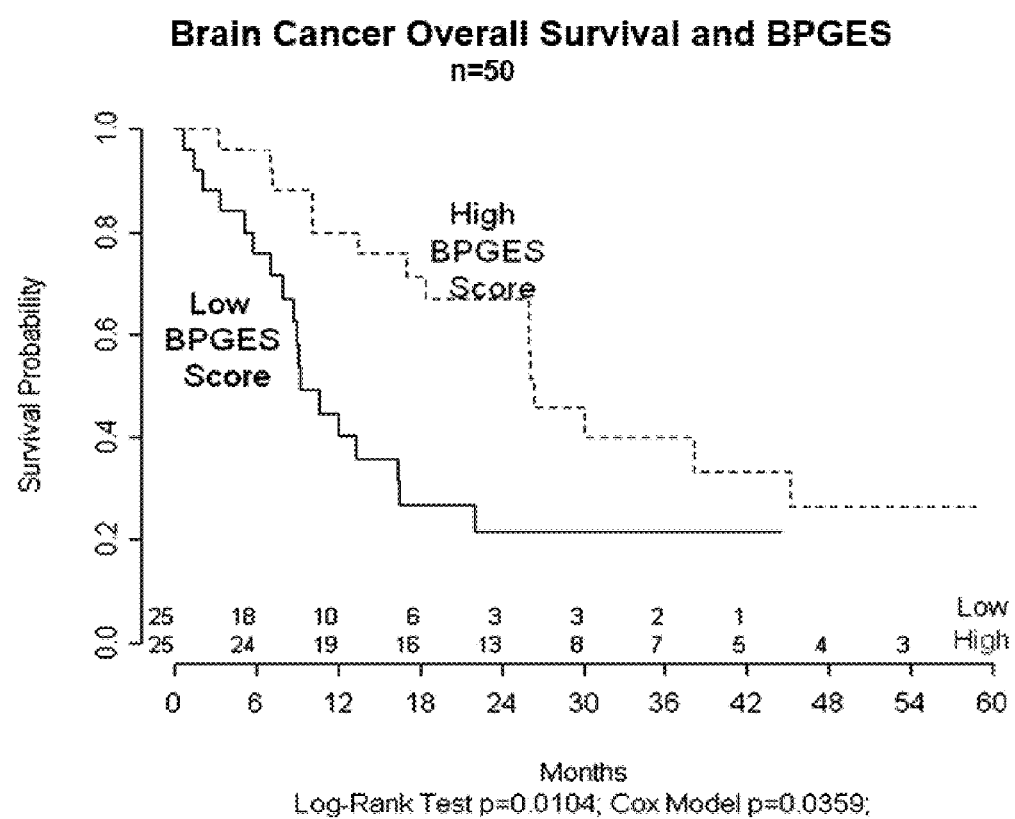
Figure 8C:
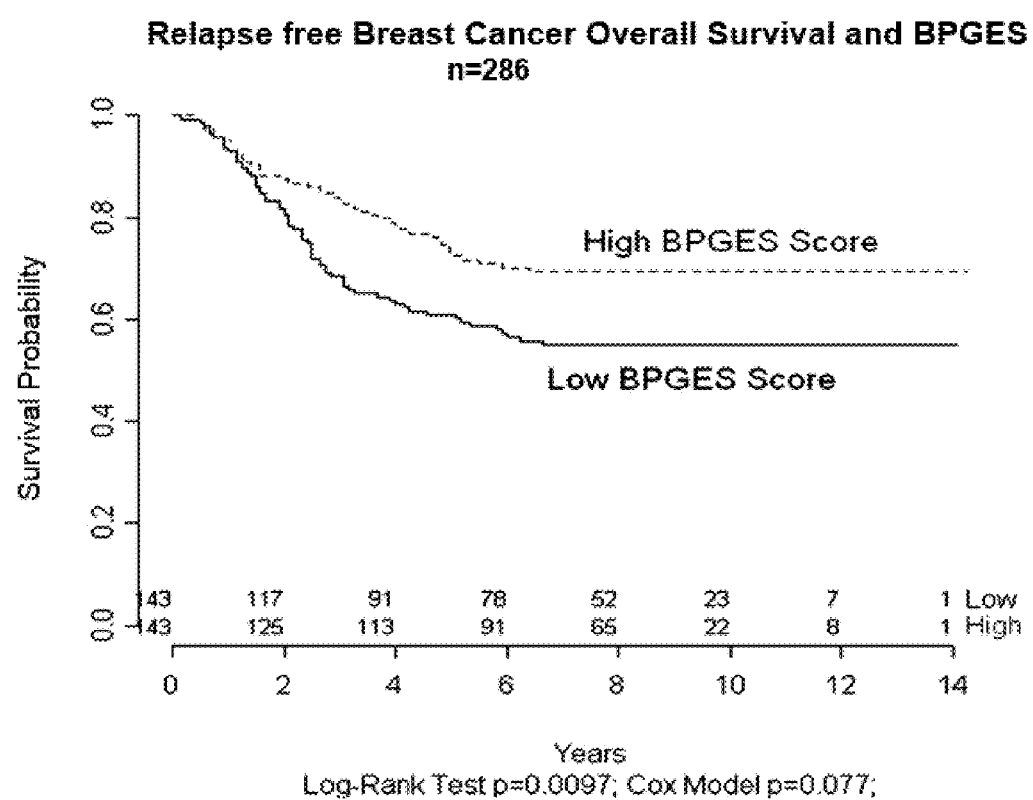
Figure 8D:
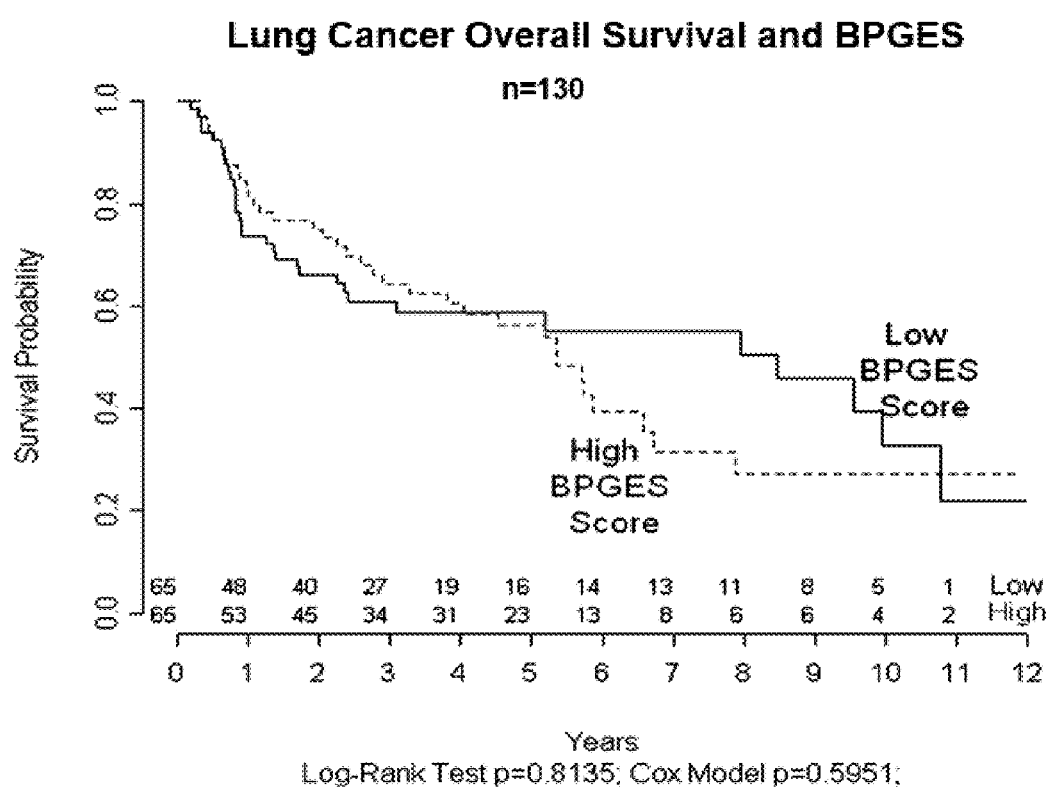
Figure 9A:
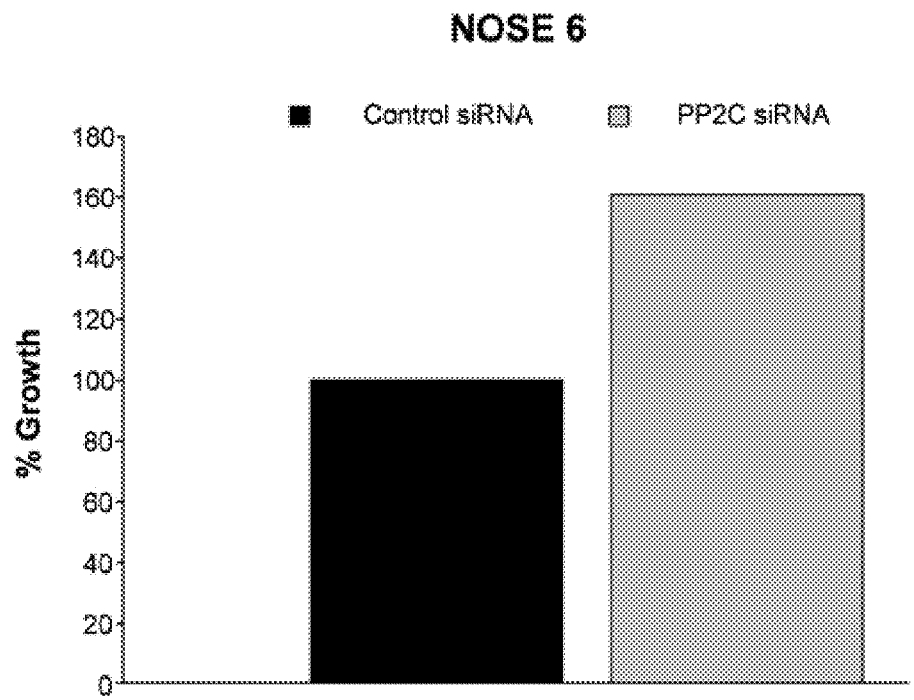
FIG. 9A-D is a series of images depicting modulation of BAD phosphorylation affects cancer cell proliferation. Depletion of the BAD protein phosphatase PP2C by siRNA resulted in increased cell proliferation in (A and B) NOSE-6 and (C and D) NOSE-7 cells. PP2C levels were confirmed by western blot.
Figure 9B:
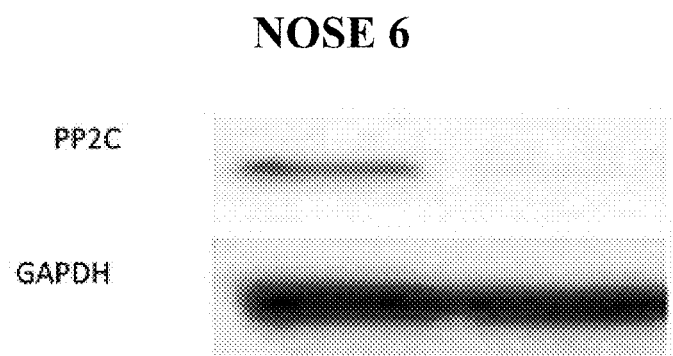
Figure 9C:
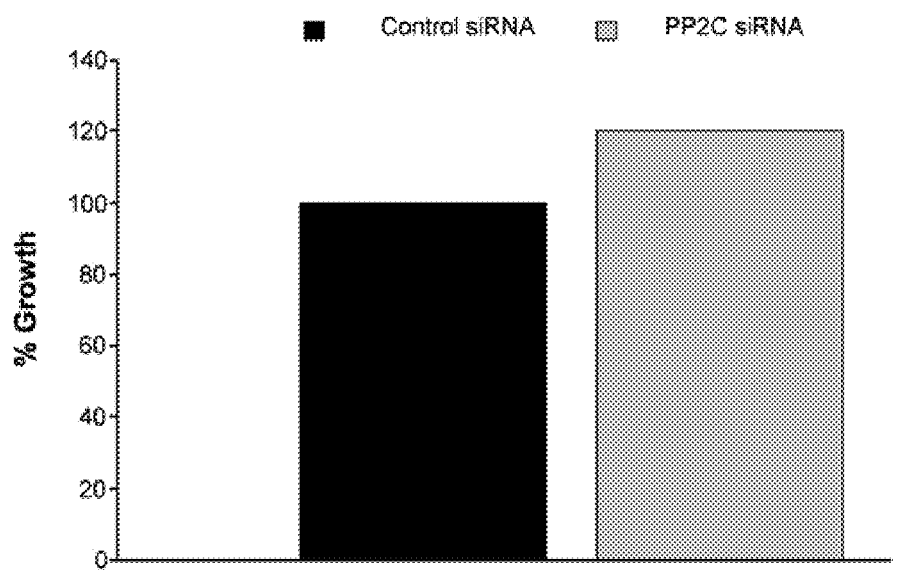
Figure 9D:
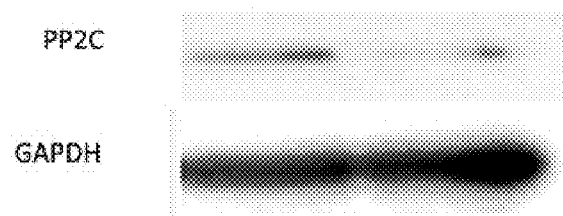

3A and B). The NSCLC set was the exception to this observation. Western blotting of the phosphorylation sites of BAD in breast, renal, ovarian, melanoma, and colon cancer in relative chemosensitive/chemoresistant cell pairs revealed higher BAD phosphorylation (consistently serine-155 and -136 levels and sporadically serine-112 levels) in more resistant cell lines among most cancer types (FIGS. 3C and D).

Modulation of BAD Phosphorylation Affects Proliferation of Cancer Cell Lines

Figure 10A:
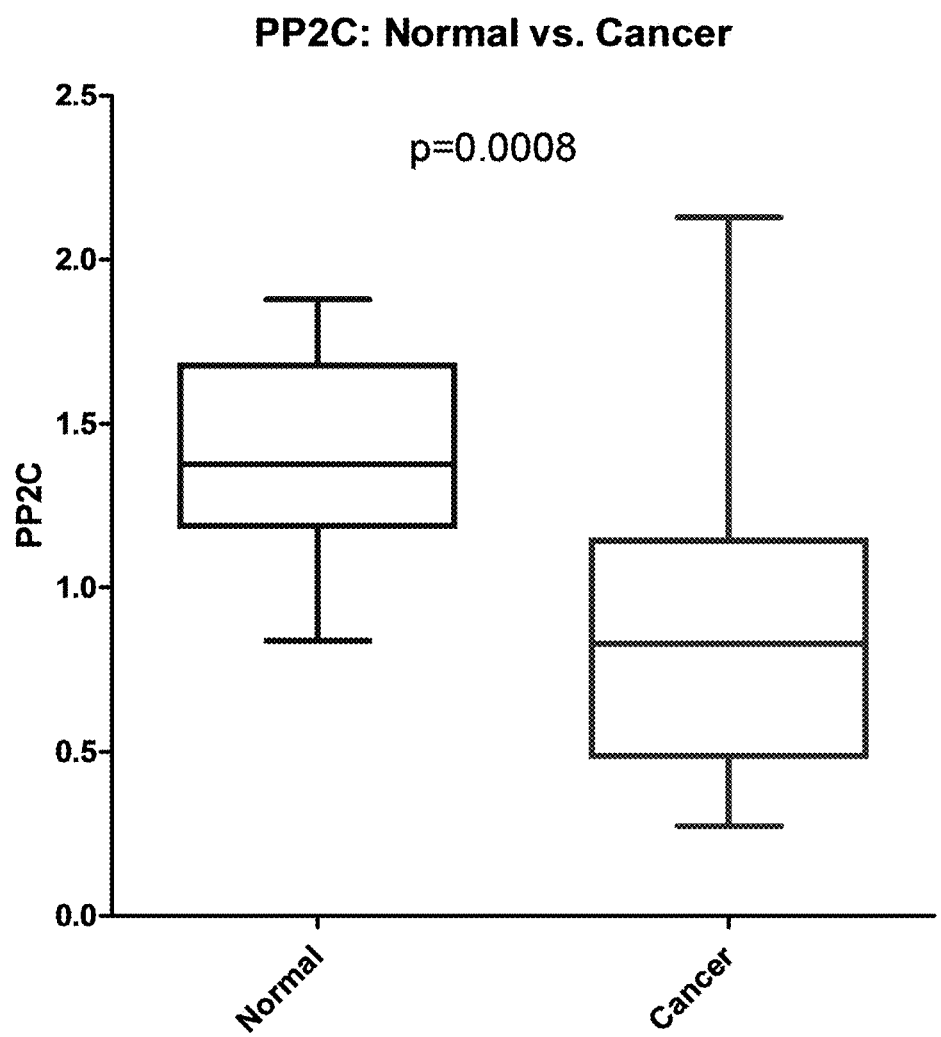
FIG. 10A-B is a series of images depicting modulation of BAD phosphorylation identifies cancer cells and affects cancer treatment susceptibility. Expression of BAD pathway phosphatase PP2C was evaluated in (A) normal versus ovarian cancer, and (B) complete versus incomplete treatment response, using quantitative PCR.
Figure 10B:
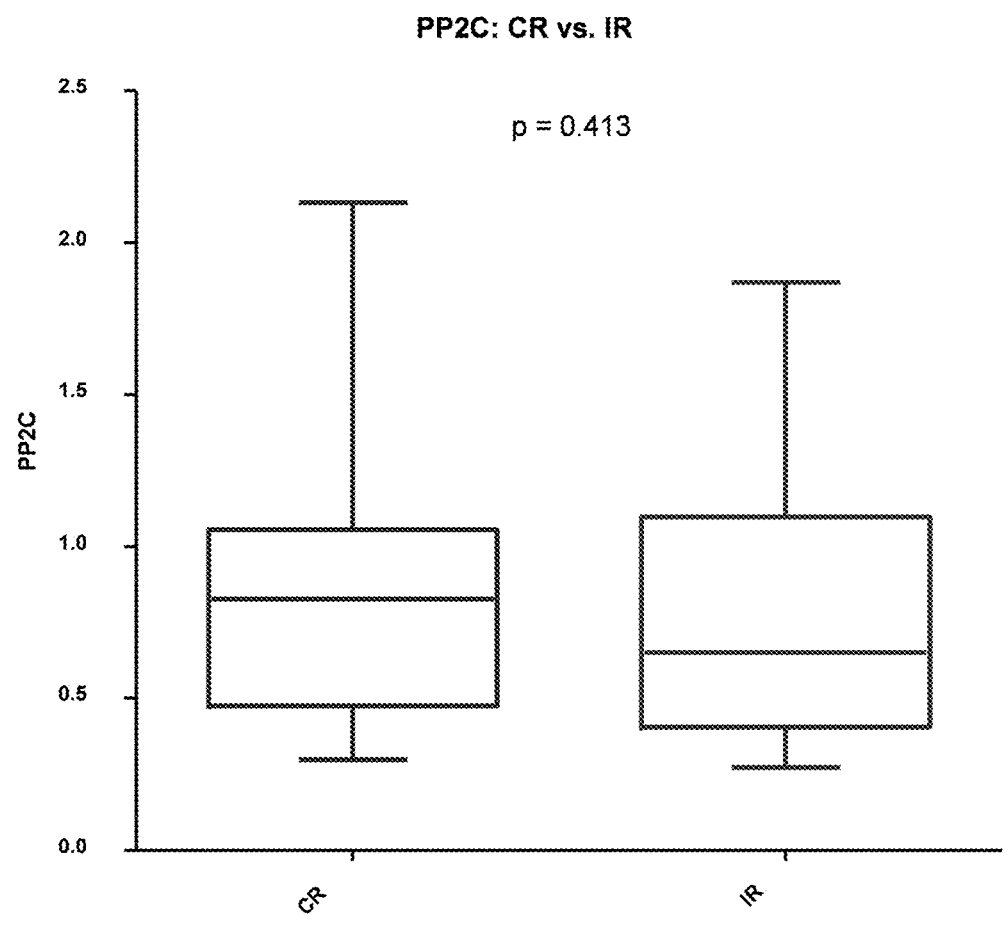

The role of pBAD in cancer cell survival and proliferation was further evaluated by depleting CDK1 and PP2C, known modulators of BAD phosphorylation, via siRNA in a panel of cancer cell lines (FIG. 4). Depletion of PP2C was confirmed by western blot, as seen in FIG. 9. Depletion of the BAD kinase, CDK1, in the breast (MCF-7), ovarian (OVCAR-4), and colon (HCT-15) cancer cell lines resulted in decreased cell proliferation of 28% in MCF-7, 27% in OVCAR-4, and 36% in HCT-15 cells (FIGS. 4A and B). In contrast, depletion of the BAD protein phosphatase, PP2C, increased cell proliferation by 11% in MCF-7 and 42% in MBA-231 breast cancer cells and 13% in HEC-1-A endometrial cancer cells (FIGS. 4C and D). Expression of BAD pathway phosphatase PP2C was evaluated using quantitative PCR in 9 normal and 67 ovarian cancer samples, as seen in FIG. 10. As seen in the figures, ovarian cancers had wider range of PP2C expression compared to normal ovaries, while being expressed at higher levels in normal ovary than ovarian cancers. Moreover, PP2C depletion conveys oncogenic potential, via modulation of phosphorylation.

BAD Phosphorylation Status and Cancer Development

Post-translational modification of BAD represents a key control point in the decision between cell survival and apoptosis. Aberrant activity of kinases such as AKT and PKA leads to BAD inactivation and resistance to cell death signaling in tumors. (Danial, BAD: undertaker by night, candyman by day. Oncogene 2008; 27 Suppl 1: S53-70). Expression levels of pBAD (serine-112, -136, and -155), total BAD, total PKA, pPKA, AKT, and pAKT were analyzed by immunofluorescence, comparing an immortalized cell line with a cancer cell line from many tissue types, including ovarian (Nose7 vs. A2780CP), colon (CRL1831 vs. HCT-15), breast (MCF10A vs. MBA-231), and lung (WI38 vs. H-460) (FIG. 5). Phosphorylation of BAD is also influenced by other kinases and phosphatases. Compared to immortalized cell lines, the cancer cell lines showed increased pBAD expression (serine-112, -136, and -155), as well as one or more kinases known to phosphorylate BAD: pPKA and pAKT. The lung set was an exception to this observation.

CONCLUSION

Collectively, the results suggest that subversion of BAD-mediated apoptosis is a key step in human cancer development and progression, an important mechanism by which tumor cells acquire resistance to therapeutic apoptotic stimuli, and a potentially useful biomarker of outcome for patients with a range of different cancers. The BAD pathway thus represents an attractive target for biomarker and therapeutic development.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall there between.

What is claimed is:

1. A method of treating ovarian cancer comprising:
obtaining a sample suspected of being cancerous or pre-cancerous from a patient;
obtaining an expression level of BAD pathway genes EGFR, SOS2, IGF1R, BAD, PRKAR1A, and YWHAZ;
determining a BAD Pathway Gene Expression Signature (BPGES) score of the sample wherein the BPGES score is determined by principal component analysis (PCA) in which $X=t_1*p_1'+t_2*p_2'+t_3*p_3'+ \ldots +t_4*p_4'+E$, where X is gene expression value, $t_i$ is score, $p_i$ is loading coefficient, and E is residual matrix;
calculating a median BPGES score using a highest and a lowest value of the expression levels of the BAD pathway genes obtained in the sample;
determining if the cancerous or pre-cancerous cells of the patient will be sensitive to carboplatin by comparing the BAD Pathway Gene Expression Signature (BPGES) score of the sample suspected of being cancerous or pre-cancerous to the median BPGES score;
wherein a high BAD Pathway Gene Expression Signature (BPGES) score as compared to the median BPGES score is indicative of chemosensitive ovarian cancer; and
administering carboplatin to the patient having the high BPGES score.

* * * * *